United States Patent [19]

Aldous et al.

[11] Patent Number: 5,665,763
[45] Date of Patent: Sep. 9, 1997

[54] THERAPEUTIC PHENOXYALKYLPYRIDAZINES AND INTERMEDIATES THEREFOR

[75] Inventors: David J. Aldous, Glenmore; Thomas R. Bailey, Phoenixville; Guy Dominic Diana; Theodore J. Nitz, both of Pottstown, all of Pa.

[73] Assignee: Sanofi, S.A., France

[21] Appl. No.: 706,109

[22] Filed: Aug. 30, 1996

Related U.S. Application Data

[62] Division of Ser. No. 461,285, Jun. 5, 1995, Pat. No. 5,567,717, which is a division of Ser. No. 242,528, May 13, 1994, Pat. No. 5,514,679.

[51] Int. Cl.$^6$ .............. A61K 31/34; A61K 31/38; C07D 307/42; C07D 409/12
[52] U.S. Cl. .............. 514/461; 514/471; 514/473; 514/444; 549/60; 549/472; 549/473; 549/474; 549/475; 549/476; 549/479; 549/491; 549/497
[58] Field of Search .............. 549/475, 476, 549/479, 491, 497, 474, 473, 472, 60; 514/471, 473, 444

[56] References Cited

U.S. PATENT DOCUMENTS

| | | | |
|---|---|---|---|
| 4,861,791 | 8/1989 | Diana et al. | 514/374 |
| 5,103,014 | 4/1992 | Musser et al. | 548/204 |
| 5,514,679 | 5/1996 | Aldous et al. | 514/247 |
| 5,567,719 | 10/1996 | Aldous et al. | 514/342 |

*Primary Examiner*—Johann Richter
*Assistant Examiner*—Laura R. Cross
*Attorney, Agent, or Firm*—Paul E. Dupont

[57] ABSTRACT

Compounds of the formula

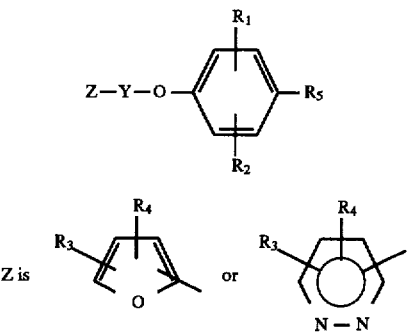

wherein:

$R_1$, $R_2$, $R_3$ and $R_4$ are as defined in the specification,

Y is alkylene of 3 to 9 carbon atoms, $R_5$ is alkoxycarbonyl, alkyltetrazolyl, phenyl or a heterocycle chosen from benzoxazolyl, benzathiazolyl, thiadiazolyl, imidazolyl, dihydroimidazolyl, oxazolyl, thiazolyl, oxadiazolyl, pyrazolyl, oxazolinyl, isoxazolyl, isothiazolyl, furyl, triazolyl, thiophenyl, pyridyl, pyrimidinyl, pyrazinyl, pyridazinyl or any of the above substituted with alkyl, alkoxyalkyl, cycloalkyl, halo alkyl, hydroxyalkyl, alkoxy, hydroxy, halo, furyl, thienyl, fluoroalkyl;

or a pharmaceutically acceptable acid addition salts thereof; N-oxides thereof, are useful as antipirconaviral agents.

7 Claims, No Drawings

THERAPEUTIC PHENOXYALKYLPYRIDAZINES AND INTERMEDIATES THEREFOR

CROSS-REFERENCE TO RELATED APPLICATIONS

This application is a division of our application Ser. No. 08/461,285, filed on Jun. 5, 1995, now U.S. Pat. No. 5,567,717, which in turn is a division of our prior application Ser. No. 08/242,528, filed on May 13, 1994 now U.S. Pat. No. 5,514,679.

BACKGROUND OF THE INVENTION a) Field of the Invention

This invention relates to novel heterocyclic substituted phenoxyalkylpyrazines, to methods of preparation thereof and to methods of use thereof as antipicornaviral agents; and to intermediates in their preparation and the use of those intermediates as antipicornaviral agents.

b) Information Disclosure Statement

U.S. Pat. No. 4,857,539 to Diana et al., issued Aug. 15, 1989, discloses compounds of the formula;

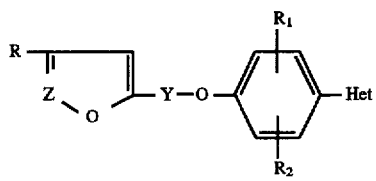

wherein:

Y is an alkylene bridge of 3–9 carbon atoms;

Z is N or HC:

R is hydrogen or lower-alkyl of 1–5 carbon atoms, with the proviso that when Z is N, R is lower-alkyl;

$R_1$ and $R_2$ are hydrogen, halogen, lower-alkyl, lower-alkoxy, nitro, lower-alkoxycarbonyl or trifluoromethyl; and Het is selected from;

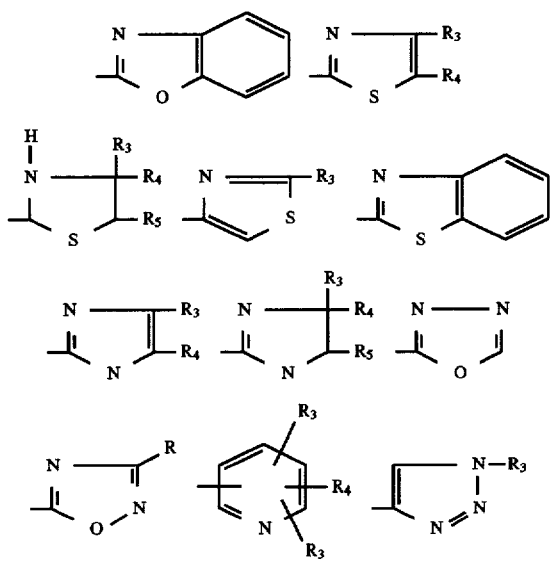

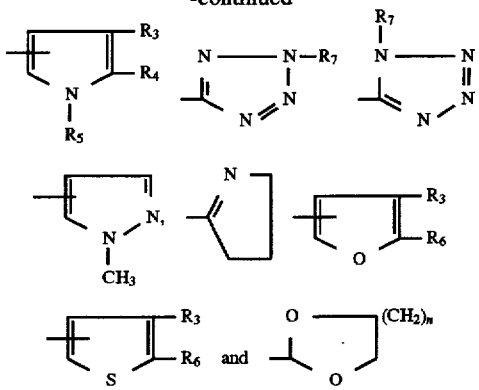

which are stated to be useful as antiviral agents.

U.S. Pat. No. 4,861,791 to Diana et al., issued Aug. 29, 1989 discloses compounds of the formula:

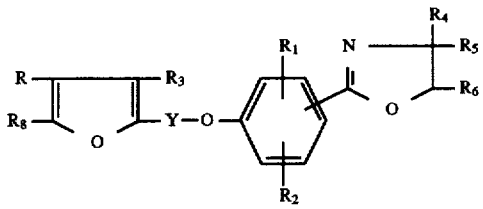

wherein R to $R_8$ represent various radicals and y. The compounds are stated to be useful as antiviral agents, in particular against picornaviruses.

U.S. Pat. No. 5,242,924, to Diana, issued Sep. 7, 1993 from application filed Jul. 2, 1992, discloses compounds of the formula:

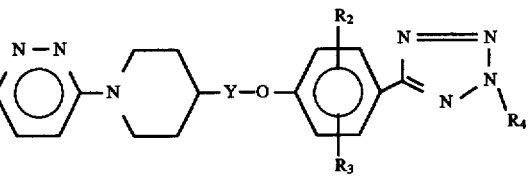

wherein

Y is a bond, or $C_1$–$C_6$ alkylene;

$R_1$ is hydrogen or $C_1$–$C_3$ lower-alkyl;

$R_2$ and $R_3$ are each independently hydrogen, $C_1$–$C_3$ lower-alkyl or halogen;

$R_4$ is hydrogen, or $C_1$–$C_3$ lower-alkyl;

or pharmaceutically acceptable acid addition salts thereof which are stated to be useful as antiviral agents, particularly against picornaviruses. antiviral European Patent Application 435381, published Jul. 3, 1991, discloses pyridazinamines of formula:

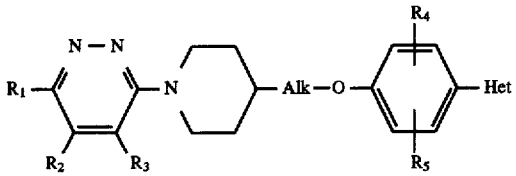

wherein $R_1$ is hydrogen, $C_{1-4}$alkyl, halo, hydroxy, trifluoromethyl, cyano, $C_{1-4}$alkoxy, $C_{1-4}$alkylthio, $C_{1-4}$alkylsulfinyl, $C_{1-4}$alkylsulfonyl, $C_{1-4}$alkyloxycarbonyl, $C_{1-4}$alkylcarbonyl or aryl;

$R_2$ and $R_3$ are hydrogen or $C_{1-4}$alkyl;

Alk is $C_{1-4}$alkanediyl;

$R_4$ and $R_5$ are hydrogen, $C_{1-4}$alkyl or halo; and Het is

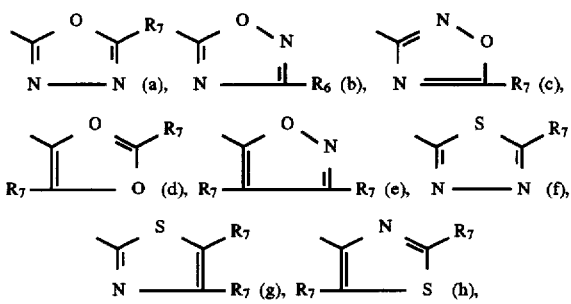

$R_6$ is hydrogen, $C_{1-6}$alkyl; hydroxy$C_{1-6}$alkyl; $C_{3-6}$cycloalkyl; aryl; aryl$C_{1-4}$alkyl; $C_{1-4}$alkyloxy$C_{1-4}$alkyl; $C_{3-6}$cyclo- alkyl$C_{1-4}$alkyl; trifluoromethyl or amino;

each $R_7$ independently is hydrogen; $C_{1-6}$alkyl; $C_{1-6}$cycloalkyl; aryl; aryl$C_{1-4}$alkyl; $C_{1-4}$alkyloxy$C_{1-4}$alkyl; $C_{3-6}$cyclo- alkyl$C_{1-4}$alkyl or trifluoromethyl; and each aryl independently is phenyl or phenyl substituted with 1 or 2 substituents each independently selected from halo, $C_{1-4}$alkyl, trifluoromethyl, $C_{1-4}$alkyloxy or hydroxy. The compounds are stated to have antiviral activity.

SUMMARY OF THE INVENTION

It has now been found that compounds of Formula I and II are effective antipicornaviral agents. Accordingly, the present invention relates to compounds of the formula;

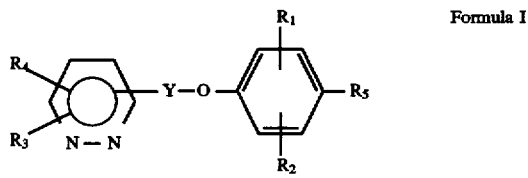

Formula I wherein:

Y is an alkylene bridge of 3–9 carbon atoms;

$R_1$ and $R_2$ are each independently chosen from hydrogen, halo, alkyl, alkenyl, amino, alkylthio, hydroxy, hydroxyalkyl, alkoxyalkyl, alkylthioalkyl, alkyl sulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ and $R_4$ are each independently chosen from hydrogen, alkyl, alkoxy, hydroxy, cycloalkyl, hydroxyalkyl, hydroxyhaloalkyl, alkoxyalkyl, hydroxyalkoxy, alkylthioalkyl, alkanoyl, alkanoyloxy, alkylsulfinylalkyl, alkylsulfonylalkyl, aminoalkyl, alkylaminoalkyl, dialkylaminoalkyl, alkoxycarbonyl, carboxy, cyanomethyl, fluoroalkyl, or halo;

$R_5$ is alkoxycarbonyl, alkyltetrazolyl, phenyl or heterocyclyl chosen from benzoxazolyl, benzathiazolyl, thiadiazolyl, imidazolyl, dihydroimidazolyl, oxazolyl, thiazolyl, oxadiazolyl, pyrazolyl, oxazolinyl, isoxazolyl, isothiazolyl, furyl, triazolyl, thiophenyl, pyridyl, pyrimidinyl, pyrazinyl, pyridazinyl or substituted heterocyclyl or substituted phenyl; wherein the substitution is with alkyl, halo, alkoxyalkyl, cycloalkyl, haloalkyl, hydroxyalkyl, alkoxy, hydroxy, furyl, thienyl or fluoroalkyl; or a pharmaceutically acceptable acid addition salt thereof.

The present invention also relates to compounds of the formula;

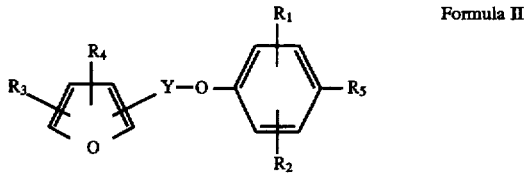

Formula II wherein:

Y is an alkylene bridge of 3–9 carbon atoms;

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ and $R_4$ are each independently chosen from is hydrogen, alkyl, alkoxy, hydroxy, cycloalkyl, hydroxyalkyl, alkoxyalkyl, hydroxyalkoxy, alkylthioalkyl, alkanoyl, alkanoyloxy, alkylsulfinylalkyl, alkylsulfonylalkyl, aminoalkyl, alkylaminoalkyl, dialkylaminoalkyl, alkoxycarbonyl, carboxy, cyanomethyl, fluoroalkyl, or halo; and $R_5$ is alkoxycarbonyl, alkyltetrazolyl, phenyl or heterocyclyl chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, thiophenyl, pyridyl, pyrimidinyl, pyrazinyl, pyridazinyl or substituted heterocyclyl or substituted phenyl; wherein the substitution is with alkyl, alkoxyalkyl, cycloalkyl, haloalkyl, hydroxyalkyl, halo, alkoxy, hydroxy, furyl, thienyl, fluoroalkyl or a pharmaceutically acceptable acid addition salts thereof.

The invention also relates to compositions for combating picornaviruses comprising an antipicornavirally effective amount of a compound of Formula I or II with a suitable carrier or diluent, and to methods of combating picornaviruses therewith, including the systemic treatment of picornaviral infections in a mammalian host.

In addition to their use as antipicornaviral agents, the compounds of formula II are useful as intermediates for preparing the compounds of formula I.

DETAILED DESCRIPTION OF PREFERRED EMBODIMENTS

Compounds of Formula I and II are useful as antipicornaviral agents, and are further described hereinbelow.

Alkyl and alkoxy refer to aliphatic radicals, including branched radicals, of from one to five carbon atoms. Thus the alkyl moiety of such radicals include, for example methyl, ethyl, propyl, isopropyl, n-butyl, sec-butyl, t-butyl, pentyl and the like. Alkoxy refers to alkyloxy, such as methoxy, pentoxy and the like.

Cycloalkyl means an alicyclic radical having from three to seven carbon atoms as illustrated by cyclopropyl, cyclobutyl, cyclopentyl, cycloheptyl, and cyclohexyl; and Halo means bromo, chloro, iodo or fluoro. Heterocyclyl or Het refers to a 5 or 6 membered carbon based heterocycle radical, having from one to about four nitrogen atoms and/or one oxygen or sulfur atom, provided that no two oxygen and/or sulfur atoms are adjacent in the heterocycle. Examples of these include furyl, oxazolyl, isoxazolyl, pyrazyl, imidazolyl, thiazolyl, tetrazolyl, thienyl, pyridyl, oxadiazolyl, thiadiazolyl, triazinyl, pyrimidinyl and the like.

The term heterocyclyl includes all known isomeric radicals of the described heterocycles unless otherwise specified, for example, thiadiazolyl encompasses 1,3,4-thiadiazol-2-yl, 1,2,4-thiadiazol-5-yl, and 1,2,4-thiadiazol-3-yl; thiazolyl encompasses 2-thiazolyl, 4-thiazolylyl and 5-thiazolyl and the other known variations of known heterocyclyl radicals. Thus any isomer of a named heterocycle radical is contemplated. These heterocycle radicals can be attached via any available nitrogen or carbon, for example, tetrazolyl contemplates 5-tetrazolyl or tetrazolyl attached via any available nitrogen of the tetrazolyl ring; furyl encompasses furyl attached via any available carbon, etc.

The preparation of such isomers are well known and well within the scope of skilled artisan in medicinal or organic chemistry.

Certain heterocycles can exist as tautomers, and the compounds as described, while not explicity describing each tautomeric form, are meant to embrace each and every tautomer. For example, pyridazin-6-ones and 6-hydroxypyridazines are tautomers. Thus the compounds of formula I depicted as hydroxypyridazines ($R_3$=OH) are understood to include the tautomeric pyridazinones.

In the use of the terms hydroxyalkyl and alkoxyalkyl, it is understood that the hydroxy and alkoxy groups can occur at any available position of the alkyl. Thus hydroxyalkyl and alkoxyalkyl include, for example, hydroxyethyl, 2-hydroxyethyl, 2- hydroxymethyl, 2-hydroxypropyl, 2-hydroxyisopropyl, 2-, 3-, 4- and 5-hydroxypentyl and the like; alkoxy refers to the corresponding alkyl ethers thereof.

In the use of the term hydroxyalkoxy, it is understood that the hydroxy group can occur at any available position of alkoxy other than the C-1 (geminal) position. Thus hydroxyalkoxy includes, for example, 2-hydroxyethoxy, 2-hydroxypropoxy, 2-hydroxyisopropoxy, 5-hydroxypentoxy and the like.

Alkylene refers to a linear or branched divalent hydrocarbon radical of from 1 to about 5 carbon atoms such as methylene, 1,2-ethylene, 1,3-propylene, 1,4-butylene, 1,5-pentylene, 1,4-(2-methyl)butylene and the like. Alkylene also includes the above group having an alkene or alkyne linkage therein.

Halogen refers to the common halogens fluorine, chlorine, bromine and iodine.

As used herein, the term haloalkyl refers to a halo substituted alkyl, such as fluoroalkyl, chlorofluoroalkyl, bromochloroalkyl, bromofluoroalkyl, bromoalkyl, iodoalkyl, chloroalkyl and the like where the haloalkyl has one or more than one of the same or different halogens substituted for a hydrogen. Examples of haloalkyl include chlorodifluoromethyl, 1-chloroethyl, 2,2,2 trichloroethyl, 1,1-dichloroethyl, 2-chloro, 1,1,1,2 tetrafluoroethyl, bromoethyl and the like.

As used herein the term fluoroalkyl is a preferred subclass of haloalkyl, and refers to fluorinated and perfluorinated alkyl, for example fluoromethyl, difluoromethyl, trifluoromethyl, 2,2,2-trifluoroethyl, 1,2-difluoroethyl, 1-fluoroethyl, 1,1-difluoroethyl, 1,1,2,3-tetrafluorobutyl and the like.

The compounds of Formula I wherein $R_5$ is a basic nitrogen containing heterocycle are sufficiently basic to form acid addition salts and are useful both in the free base form and the form of acid-addition salts, and both forms are within the purview of the invention. The acid-addition salts are, in some cases, a more convenient form for use, and in practice the choice of use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds can be prepared by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or by concentration of the solution or by any one of several other known methods. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC) or other art accepted means.

As described herein a noninteracting solvent can be N-methyl pyrrolidinone (NMP), methylene chloride ($CH_2Cl_2$), tetrahydrofuran (THF), benzene or any other solvent that will not take part in the reaction. In a preferred method, the preparation of compounds of the invention is done in dried solvents under an inert atmosphere. Certain reagents used in example preparations are specified by abbreviation: triphenylphosphine (TPP), m-chloroperbenzoic acid (MCPBA) triethylamine (TEA), diisopropylethylamine (DIPEA), and diethyl azodicarboxylate (DEAD). Ether is diethyl ether unless otherwise specified.

Compounds of Formula I can be prepared by several different methods:

Compounds of formula I can be prepared by the reaction of the appropriate hydroxyalkyl furan and the appropriate $R_1$—$R_{2-4}$—$R_5$-phenol, as described in U.S. Pat. No. 5,242,924, and 5,051,437 incorporated herein by reference, giving a compound of formula II. The compound of formula II is then reacted with a peroxide, such as m-chloroperbenzoic acid (MCPBA) and then reacted with hydrazine, providing a compound of formula I.

Compounds of formula I can also be prepared by reaction of the appropriate $R_1$—$R_{2-4}$—$R_5$-phenol and the appropriate furanylalkylhalide as described in U.S. Pat. No. 4,942,241, incorporated herein by reference, to form a compound of formula II which is then treated with an oxidizing agent such as dimethyldioxirane, MMPA or MCPBA and then reacting this oxidized intermediate with hydrazine as described above.

A compound of formula I can be prepared from a $R_1$—$R_{2-4}$—$R_5$-Phenol and ω-pyrazinyl alkynol (wherein the alkyne linkage preferably is proximal to the pyridazine ring) by the reaction methods disclosed in U.S. Pat. No. 5,242,924 incorporated herein by reference. Such compounds of formula I have an alkynyl linkage in Y, the alkylene bridge. These linkages can be partially reduced to yield alkenyl linkages or reduced to provide a preferred saturated alkylene bridge.

Compounds of formula II wherein $R_5$ is heterocyclyl can be prepared by the reaction of a hydroxyalkyl furan or furanylalkylhalide with a $R_1$—$R_{2-4}$-functionalized phenol. The 4-substituted is then converted to the heterocycle as described hereinbelow.

Likewise, compounds of formula I wherein $R_5$ is heterocyclyl can be prepared by reaction of the $R_1$—$R_{2-4}$-functionalized phenol and a ω-pyridazyl alkynol, then elaboration of the $R_5$ heterocycle deferred to the final steps of the synthesis.

For example, if $R_5$ is a heterocyclic ring, the heterocycle can be elaborated or substituted on to the phenyl ring by means of the appropriate 4-functionalized phenoxyalkyl furan or pyridazine. In this method, the heterocycle on the phenoxy ring can be elaborated in the final step to yield a compound of formula II or formula I as described in U.S. Pat. No. 5,075,187 incorporated herein by reference. Suitable functionalization of the 4-phenoxy position will depend upon the heterocycle sought in the final product. (It will be understood that this method, when applied to a suitably protected 4-functionalized phenol, the product is a suitably protected $R_1$—$R_{2-4}$-heterocyclyl phenol, which can then be deprotected. The resulting phenol is then used to prepare a compound of formula I or II.)

For example, where Het is 1,2,4-oxadiazolyl

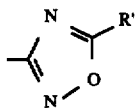

compounds are prepared from either the appropriate 4-Z—O—$R_1$—$R_2$-benzonitrile (where z is alkyl or benzyl if the target compound is a phenol intermediate), where z is —Y-furan if the target compound is the compound of formula II, or when z is —Y-pyridazine if the target compound is a compound of formula I. The benzonitrile is reacted with, for example, hydroxylamine hydrochloride in a noninteracting solvent, preferably an alkanol, for example; methanol, ethanol, n-butanol and the like, in the presence of a base, such as potassium carbonate, or in a preferred method, an alkali metal salt of a carboxylic acid such as sodium trifluoroacetate or sodium acetate, at a temperature between ambient and the boiling point of the solvent. The product thus obtained can then be reacted with for example an acid anhydride of formula (R'CO)$_2$O, (where R' is alkyl, haloalkyl and the like), for example, trifluoroacetic anhydride, or acetic anhydride, at a temperature between ambient temperature and the boiling point of the reaction mixture in a basic solvent such as pyridine. The R' appears on the $R_5$ of the product. The product of the reaction is a 4-ZOR$_1$—$R_2$-phenyloxadiazole, where the starting material is the 4-ZO—$R_1$—$R_2$-benzonitrile. The product is a compound of formula II where the starting material is the 4-cyanophenoxyalkylfuran (or formula I where 4-cyanophenoxyalkyl pyridazine issued; or a suitably protected 4-heterocyclyl phenol, if Z is a protective group).

Alternatively, the compounds of formula I and II can be prepared by reaction of a $R_1$—$R_2$—$R_5$-phenol with, for example, an ω-functionalized haloalkane. The resulting (ω-functionalized alkoxy-$R_1$—$R_2$—$R_5$-phenyl moiety is then reacted with a suitably functionalized furan or pyridazine to provide compounds of formula II or formula I respectively. This method for preparing compounds of the invention is analogous to the preparation of furanyl alkylhalides, hydroxyalkylfurans, and ω-pyridazyl alkynols discussed hereinbelow.

Thus it will be appreciated that neither the timing of the elaboration of the heterocyclic substituents or pyridazine nor the order of assembly of the intermediate; is crucial to the successful synthesis of compounds of Formula I or II. By judicious choice of reactants one can prepare any of the compounds of Formula I or II. The $R_1$—$R_{2-4}$—$R_5$-phenols used to prepare compounds of Formula I and of Formula II wherein $R_5$=heterocyclyl or alkoxycarbonyl are known in the art. Their preparation is described in U.S. Pat. No. 4,942,241; 4,945,164; 5,051,437; 5,002,960; 5,110,821; 4,939,267; 4,861,971; 4,857,539; 5,242,924; or 4,843,087 incorporated herein by reference. Any 4-alkoxycarbonyl phenol or any 4-heterocyclyl phenol disclosed in these patents, or others which are known in the art, can be reacted with a hydroxyalkylfuran or furanyl alkylhalide by the methods described (or incorporated above) to prepare compounds of formula II, which can be elaborated to pyridazines of formula I. $R_1$—$R_2$—$R_5$-phenols can be reacted with pyridazine alkynols, to form compounds of formula I directly. Other known phenols can be used to prepare compounds of formula I or II, including for example any 4-phenyl phenol, or 4-alkoxyphenol, substituted or unsubstituted as described above, each is well known and useful.

$R_1$—$R_{2-4}$—$R_5$-phenols wherein $R_5$ is heterocyclyl can be prepared from the suitably protected phenol, such as the phenoxyalkyl ether or phenoxybenzyl ether which has been suitably functionalized at the 4-position by a functional group such as cyanide, aldehyde, halide, acetyl, acid chloride group or other suitable functional group, as described in U.S. Pat. Nos. 4,942,241; 4,945,164; 5,051,437; 5,002,960; 5,110,821; 4,939,267; 4,861,971; 4,857,539; 5,242,924; or 4,843,087 each incorporated herein by reference, to obtain the heterocyclyl phenoxyalkyl ether or heterocyclyl phenoxybenzyl ether which is then cleaved to the corresponding phenol by means well known in the art.

It is preferred for certain $R_5$ heterocycles that they be attached to a suitably protected phenol precursor by standard coupling methods. For example, when $R_5$ is pyrimidyl, phenyl, pyridyl and the like, a protected $R_1$—$R_{2-4}$-hydroxyphenyl borate can be reacted with a haloheterocycle, such as bromopyridine, to prepare a suitably protected 4-pyridyl phenol, which is then deprotected, to liberate the pyridyl phenol.

The skilled practitioner will realize certain heterocyclyls, such as oxazolyl, oxadiazolyl and the like are easiest prepared by elaborating functional groups attached to the phenol, thus forming the $R_5$ heterocycle "in situ" rather than attaching it to the phenol or suitably protected phenol. This method of preparing $R_5$ heterocycles is also applicable to 4-functionalized phenoxyalkyl furans and 4-functionalized phenoxy alkyl pyridazines, which upon elaboration of the $R_5$ heterocycle are compounds of formula II and I respectively.

Furanyl alkyl halides and hydroxyalkyl furans are known, or prepared by known methods. See Katritsky and Rees,

*Comprehensive Heterocyclic Chemistry*, Vol. 14. Useful starting materials in the preparation of hydroxyalkyl furans and furanyl alkylhalides, as well as compounds of formula II are furans. As described above, the furanyl radical can be attached via any available carbon on the furanyl ring to the Y moiety (the alkylene bridge portion of the molecule). Many furans are commercially available, such as 2-furaldehyde, 3-furaldehyde, 3-furaldehyde diethyl acetal, 2-furaldehyde dimethyl hydrazone, 2-furanyl acrolein, 2-furylacrylic acid, 3-furylacrylic acid, 2-furanacrylonitrile, 2,5-furan dimethanol, furfuryl alcohol, furfuryl mercaptan, 3-furan methanol, furfuryl acetate. These and other known furans can be functionalized by known methods. The preparation of the ω-hydroxy or ω-haloalkyl furans are described in U.S. Pat. Nos. 4,942,241; 4,945,164; 5,051,437; 5,002,960; 5,110,821; 4,939,267; 4,861,971; 4,857,539; 5,242,924; or 4,843,087 incorporated herein by reference. These processes are useful for preparing the hydroxyalkyl furans and furanyl alkylhalide intermediates, as well as in preparing compounds of formula II directly.

Pyridazine alkynols can be prepared by any known method. A preferred method of forming the alkynol is by the reaction of a suitably protected ω-alkyn-1-ol with the appropriate halo, hydroxy or other suitably functionalized pyridazine, for example, under Heck conditions (PdCl$_2$(PØ$_3$)$_2$, CuI, base such as Et$_3$N), or using known tin coupling chemistry. Where R$_3$ is halo, this method is particularly useful as the product has the halide present and need not be added later.

Of course other useful starting materials in the preparation of ω-pyridazinylalkynols, pyridazinyl alkyl halides and of course, compounds of formula I are pyridazines. As described above, the pyridazinyl radical can be attached via any available carbon on the pyridazinyl ring to the Y moiety (the alkylene bridge portion of the molecule). Many pyridazines are commercially available, others are known or can be prepared by known methods, and they can be functionalized by known methods. See for example, Katritzky and Rees *Comprehensive Heterocyclic Chemistry*, Vol 3, and Castle *Heterocyclic Compounds* Vol 27–28. Pyridazine species may be reacted with terminally unsaturated species, other than alkynes and alkanols. For example, a tin-pyridazyl species can be reacted with an acrylic ester, which can later be reduced to the alkanol and then used to prepare compounds of formula I.

The pyridazines described above are commercially available, known or are prepared by known methods. For example, they may be formed directly by ring closure reactions especially preferred reactions provide pyridazinones which can be used to prepare a host of intermediates or compounds of formula I. 6-hydroxy pyridazines are prepared by known methods, for example the reaction of a zinc/β iodoester and an ω-R$_1$—R$_2$—R$_3$-phenoxy acylhalide or a ω-protected acylhalide which forms a γ-dione which is elaborated to the pyridazine by reaction of hydrazine. Such pyridazines are useful in preparing final products or intermediate compounds of formula I wherein R$_3$ is halo, thio, sulfinyl, sulfonyl, alkoxy, alkanoyloxy.

Where R$_3$ is halo, other than fluoro, it is preferred to react the ω-pyridazine alkyn-1-ol with the heterocyclyl phenol and if desired to reduce the alkynyl linkage after ether formation. The skilled artisan will also appreciate the advantage of reacting the phenol with the alkyn-1-ol before the pyridazine is attached. The advantage in protecting the alcohol functionality of the alkyn-1-ol is that any unwanted side reactions of the alcohol with the [1] deficient ring are avoided. This method advantageously provides for a more "flexible" synthetic route to many different products.

Where R$_3$ is hydroxy, these are preferably prepared from the appropriate ω-(hydroxy furan) alkanol preferably wherein the alkanol has already been suitably protected, by protecting the hydroxy on the furan ring. This can be done by reaction of the furan with dimethyldioxirane to form the 2-hydroxy-5,6-dihydro-5-pyran-5-on-2-yl compound. If the alkanol has been protected, it is deprotected and reacted with the R$_1$—R$_2$—R$_5$-phenol or R$_1$—R$_{2-4}$-functionalized phenol. The resulting compound can be reacted with hydrazine to yield the corresponding hydroxypyridazine compound.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; alkylation of phenyl or furyl substituents; preparation of thionyls from carbonyls; cleavage of alkyl or benzyl ethers to produce the corresponding alcohols or phenols; and hydrolysis of esters or amides to produce the corresponding acids, alcohols or amines, the preparation of fluoroalkyls from corresponding alkanols and ketones; oxidation of hydroxyls to carbonyls, oxidation of thiols to sulfinyls to sulfonyls, preparation of anhydrides, acid halides, aldehydes, simple aromatic alkylation and the like as desired can be carried out.

Moreover, it will be appreciated that obtaining the desired product by some reactions will be better facilitated by blocking or rendering certain functional groups non reactive. This practice is well recognized in the art, see for example, Theodora Greene, *Protective Groups in Organic Synthesis* (1991). Thus when reaction conditions are such that they can cause undesired reactions with other parts of the molecule, the skilled artisan will appreciate the need to protect these reactive regions of the molecule and act accordingly.

Starting materials used to prepare the compounds of Formula I are commercially available, known in the art, or prepared by known methods. Many of the preparations of starting materials herein are incorporated by reference from the patent literature.

EXEMPLARY DISCLOSURE

For the purpose of naming substituents in Formula I, the phenyl ring of any compound of formula I shall be numbered;

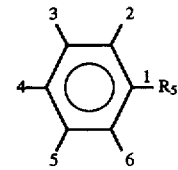

Thus when a compound of formula I has substitution on the phenyl ring, it is referred to by this numbering system regardless of how the compound may be named. For example, if a compound is prepared and the designation R$_1$,R$_2$=3,5-dimethyl, this means

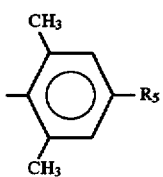

regardless of whether 3,5-dimethyl or 2,6-dimethyl appears the name of the compound.

For the purpose of naming substituents in compounds of formula I the pyridazine ring of any compound of formula I shall be numbered:

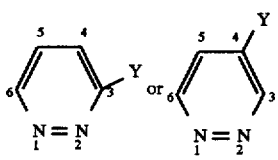

Thus when a compound of formula I has a substituted pyridazine ring, substitution thereof is referred to by the numbering system above regardless of how the compound might otherwise be named, for example;

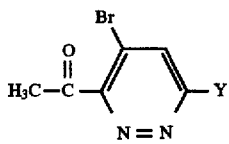

is denoted ($R_3$=5-bromo, $R_4$=6-acetyl) and not ($R_3$=3-bromo; $R_4$=2-acetyl) regardless of how the compound might properly be named by IUPAC or other commonly used nomenclature conventions.

Likewise, for the purpose of naming substituents attached to the furan in compounds of formula II, the furan ring is numbered;

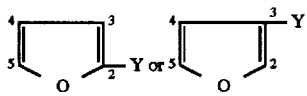

Thus when a compound has substitution on the furanyl ring, it is referred to by this numbering system when describing the compound of formula I regardless of how the compound may be named for other purposes. For example,

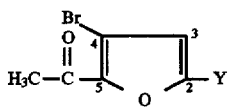

is a 2-furanyl compound with $R_3$=5-acetyl and $R_4$=4-bromo, regardless of whether the conventional name is 2-acetyl-3-bromo-5-(Y) furan or 5-acetyl-4-bromo-2-Y-furan.

Preparation of Intermediate

Intermediate 1 methyl 3-(5-ethyl-2-furanyl)prop-2-enoate a) To a solution of trimethylphosphonoacetate (16.2 g; 89 mmol) in 200 mL of THF cooled to −78° C. under nitrogen with stirring 89 mL (89 mmol) of lithium bis(trimethylsilyl) amide was added dropwise over a ½ h period. The reaction mixture was stirred continuously at −78° C. for 1 hr. To the mixture was added 10 g (81 mmol) of 2-ethyl-5-furfural and 3 mL of THF over a 10 min period with stirring. After ½ hr, stirring was stopped and the reaction mixture was allowed to stand for 3 days. An aqueous solution of saturated ammonium chloride was added to a gel like solid with stirring, and 20 mL of water was added to dissolve the precipitated salts into solution. The organic layer was separated, washed with 300 mL water, 300 mL brine, dried over anhydrous magnesium sulfate, filtered, and concentrated in vacuo to yield 20 g of crude product. The product was passed through silica gel and eluted with hexane (400 mL), ethyl acetate/hexane (1:9) (200 mL), and ethyl acetate/hexane (2:8), and the appropriate fractions were concentrated in vacuo to afford 14.8 g of methyl 3-(5-ethyl-2-furyl)propenoate.

b) methyl 3-(5-ethyl-2-furanyl)propionate

To a suspension of ethanol (200 mL) and 300 mg of 5% palladium on carbon was added 14.8 g (82.1 mmol) of 3-(5-ethyl-2-furanyl)propenoate at room temperature and the mixture was placed on a Paar hydrogenator and hydrogenated with $H_2$. Palladium on carbon was filtered off bypassing the reaction mixture through a filter aid, Super-Cel™ and the residue was washed with ethanol several times. The filtrate was concentrated in vacuo, methylene chloride was added to the residue and the solvent was removed in vacuo to afford 14.9 g methyl 3-(5-ethyl-2-furanyl)propanoate. This ester was used without further purification.

3-(5-ethyl-2-furanyl)propan-1-ol c) To a mixture of 3.42 g (90.1 mmol) of LAH in THF under nitrogen and stirring at 0° C., was added dropwise 14.9 g (81.9 mmol) of methyl 3-(5-ethyl-2-furyl)propanoate in THF. The reaction mixture was quenched with 3.4 mL of water, 3.4 mL of sodium hydroxide solution, and 10.2 mL of water. Magnesium sulfate was added to the mixture with stirring, filtered and concentrated in vacuo. The residue was passed through silica gel and eluted with ethyl acetate/hexane (2:8) to yield 10.7 g (85%) of the desired product as a clear colorless oil, used in the next preparation without further purification.

Intermediate 2

1-chloro-3-(2-furanyl)propane a) To 16 mL of furan (0.208 mol) in 300 mL of THF, cooled to −78° C., was added 100 mL of n-butyllithium in hexane (2.5M), and then 71 mL(0.4081 mol) of hexamethylphosphoramide (HMPA), 22 mL (0.2148 mol) 1-bromo-3-chloropropane and 120 mL of THF were slowly added to the above mixture. The reaction mixture was warmed to room temperature and allowed to react overnight.

The above reaction mixture was partitioned between water (250 mL and ethyl acetate (250 mL), and the aqueous layer was extracted with ethyl acetate (200 mL). The combined organic layer was washed with water (2×100 mL) and brine (200 mL), dried (MgSO$_4$), and concentrated in vacuo to afford a brown oil.

The oil was distilled under diminished pressure (0.05–0.1 mm) to afford 11.106 g (37%) of 5-(3-chloropropyl)furan.

Intermediate 3 a) 2-furanyl-2-methyl-1,3-dioxolane

A mixture of 4 mL (139.6 mmol) 2-acetylfuran, 8.7 mL (156 mmol) of ethylene glycol, 198 mg (1 mmol) of p-toluenesulfonic acid monohydrate, and 22 mL (132.3 mmol) of triethyl orthoformate was reacted at room temperature under $N_2$ for 3 days. The reaction mixture was poured into a mixture of ethyl acetate (100 mL) and water (100 mL). The aqueous layer was extracted with ethyl acetate (3×50 mL), and the combined organic layer was washed with water (100 mL), sodium bicarbonate solution (150 mL), and brine (100 mL). The organic layer was dried over MgSO$_4$, concentrated in vacuo, and the residue was distilled under reduced pressure (1.5 torr) to afford 9.98 g (50%) of 2-(2-methyl-1,3-dioxolan-2-yl)-furan, as a clear oil, b.p. 24° C./1.5 mm.

b) 5 2-[5-(3-chloropropyl)-2-furanyl]-2-methyl-1,3-dioxolane

To 9.98 g (64.74 mmol) of 2-furanyl-2-methyl-1,3-dioxolane in 125 mL of THF, cooled to −78° C., was added 46 mL (78.2 mmol) of t-butyllithium in hexane (2.5M) while maintaining the reaction temperature below −60° C., and then 23 mL (132.2 mmol) of hexamethylphosphoramide (HMPA), 7 mL (68.35 mmol) of 3-bromopropyl chloride in 100 mL of THF were slowly added to the above mixture at or below −60° C. After addition reaction mixture allowed to come to room temperature overnight. The above reaction mixture was poured into water (100 mL), and the aqueous layer was extracted with ether (100 mL). The organic layer was washed with water (5×100 mL) and brine (100 mL), and concentrated in vacuo. The residue contaminants were distilled away under vacuum (1.5 torr 23°–93° C.) to afford 7 g (46%) of the described compound.

Intermediate 4 a) Methyl 3-(5-propyl-2-furanyl)prop-2-enoate

To a solution of trimethylphosphonoacetate (13.09 mL; 66 mmol) in 500 mL of THF cooled to −78° C. under nitrogen with stirring, 132 mL (61.6 mmol) of 0.5M potassium bis(trimethylsilyl)amide in toluene was added dropwise over a ½ h period. The reaction mixture was stirred continuously at −78° C. for 1 hr. To the mixture was added 6.66 g (66 mmol) of 5-propylfuryl-2-carboxaldehyde and 3 mL of THF over a 10 min period with stirring. After 1 h, stirring was stopped and the reaction mixture was allowed to warm to room temperature over a 2 h period. The reaction mixture was quenched with an aqueous solution of saturated ammonium chloride with stirring, and water was added to dissolve the precipitated salts into solution. The THF/aqueous solution was washed with ether (200 mL), and the aqueous layer was washed again with 100 mL of ether. The combined organic layer was washed with brine, dried over anhydrous magnesium sulfate, filtered, and concentrated in vacuo and distilled (130°–135° C./16 mm) to yield 8 g (87.9%) of methyl-3-(5-methyl-2-furanyl)prop-2-enoate.

b) Methyl 3-(5-propyl-2-furanyl)propionate

A mixture of ethyl methyl-3-(5-methyl-2-furanyl)prop-2-enoate (8 g) in methanol (200 mL) and 1.5 g of 5% palladium on carbon was placed on a Paar hydrogenator and hydrogenated with H$_2$. Palladium on carbon was filtered off by passing the reaction mixture through Super-Cel™ (filter agent) and the residue was washed with ethanol. The filtrate was concentrated in vacuo to yield 8 g of methyl 3-(5-propyl-2-furanyl)propionate.

c) 3-(5-methyl-2-furyl)propan-1-ol

To a solution of methyl 3-(5-methyl-2-furanyl)propionate (3.6 g, 20 mmol) in 50 mL of THF at 0° C. was added dropwise under nitrogen 8 mL of diisobutylaluminum hydride (1M in hexane), and the mixture was stirred at room temperature over-night. The resulting solution was diluted with 2 mL of water in 10 mL of THF and brine, and the mixture was stirred for 30 min. The solid was removed by filtration, and the filtrate was diluted with 20 mL of water, extracted with methylene chloride. The organic layer was washed with water, dried over magnesium sulfate, and concentrated in vacuo. The residue was purified by passing through MPLC column (ethyl acetate/hexane) to afford 1.11 g of 3-(5-methyl-2-furyl)propan-1-ol.

Intermediate 5

Preparation of 2-methyl-5-(4-hydroxyphenyl)tetrazole a) A mixture containing 325 g of 4-cyanophenol, 346 mL of benzyl chloride and 758 g of potassium carbonate in 1.2 L of NMP was heated at 95° C. with stirring for 1.5 hrs. The reaction mixture was cooled to room temperature and poured into 5 L of cold water. The resulting white solid was collected, washed with water and hexanes and dried at 70° C. in vacuo giving 570.0 g of 4-benzyloxybenzonitrile.

b) A mixture of 285 g of the nitrile, 262.5 g triethylamine hydrochloride and 124 g of sodium azide 1.5 L of DMF under nitrogen was stirred under reflux for 18 hrs. The reaction mixture was cooled to room temperature, poured into 4 L of cold water and acidified with 3N HCl. The resulting white solid was collected, washed with water and dried at 60° C. in vacuo for 48 hrs to give 337 g of 5-(4-benzyloxyphenyl)-tetrazole.

c) To a stirred solution containing 337 g of the tetrazole and 362 mL of DIPEA in 1 L of NMP cooled to 18° C. under N$_2$ was added dropwise over 1.5 hrs 200 g of methyl iodide in 170 mL NMP. After stirring an additional hour at room temperature, the reaction mixture was diluted with 340 mL of water and cooled to 18° C. The resulting solid was collected, washed with water, recrystallized from ethanol and dried in vacuo at 50° C. to give 232.3 g of 2-methyl-5-(4-benzyloryphenyl)tetrazole.

d) A mixture containing 214.2 g of the methyl tetrazole, 140 mL of concentrated hydrochloric acid and 1.08 L of glacial acetic acid was heated under reflux for 19 hrs. Most of the acetic acid was removed by evaporation under reduced pressure at 60° C. and the resulting slurry was diluted with 1.5 L of cold water. The resulting solid was collected, washed with water and dried. Recrystallization from ethanol afforded, after drying at 60° C. for 20 hrs, 104.3 g of 2-methyl-5-(4-hydroxyphenyl)tetrazole.

Intermediate 6

Preparation of 2-methyl-5-(3,5-dlmethyl-4-hydroryphenyl)tetrazole was prepared by the procedure described above for Intermediate 5 starting with 2,6-dimethyl-4-cyanophenol.

Intermediate 7

3-(3,5-Difluoro-4-hydroxyphenyl)-5-trifluoromethyl-1,2,4,-oxadiazole 0.1 mol 3, 5-difluoro-4-methoxybenzonitrile, 0.3 mL of hydroxylamine hydrochloride and 0.3 mol of potassium carbonate were added to 400 mL ethanol and refluxed overnight. The product was filtered and recrystallized from methanol giving 3.04 g of 3,5-difluoro-4-methoxybenzamide oxime. This product was dissolved in 5 mL pyridine and 5.6 mL of trifluoroacetic anhydride was added dropwise at room temperature. Upon cooling the product solidified and was rinsed with water yielding 4.1 g of the product.

Intermediate 8

3-(4-hydroxyphenyl)-5-trifluoromethyl-1,2,4- oxadiazole 13.32 g (0.1 mol) 4-methoxybenzonitrile, 20.85 g (0.3 mol) of hydroxylamine hydrochloride and 41.40 g (0.3 mol) potassium carbonate was added to 400 mL absolute ethanol and refluxed 21 hours. The product was filtered and recrystallized from methanol to give 3.12 g (0.02 mol) of 4-methoxybenzamide oxime.

This product was dissolved in 5 mL pyridine and 5.7 mL (0.04 mol) of trifluoroacetic anhydride was added dropwise at room temperature. Upon cooling, the mixture solidified and was rinsed with water yielding 4.3 g of a product wherein $R_1=R_2=$hydrogen; $R_5=$5-trifluoromethyl-oxadiazol-3-yl.

Intermediate 9

0.384 g of 4-hydroxy-3,5-dimethyl borate and 4 mL 2M $Na_2CO_3$ in methanol and 0.4 mL of 2-chloropyridine was combined in 35 mL toluene. 0.260 g $(P\phi_3)_4Pd$ was added and the mixture was refluxed for 24 hours. The mixture was purified by MPLC in ethyl acetate and hexane. The resultant methoxy phenyl compounds taken up in 25 mL $CH_2Cl_2$ and 3.8 mL of $BBr_3$ added, and the mixture stood overnight. The mixture was diluted with 400 mL $CH_2Cl_2$ and extracted with brine, dried and concentrated in vacuo giving 1.38 g (37%) 4-(2-pyridyl) 2,6-dimethylphenol.

The following phenols were made using the above procedure but substituting the appropriate $R_5X$ species.

| $R_5$ | Z | Yield | M.P. |
|---|---|---|---|
| 4 pyrimidyl | Br | 42% | 89.5 (wet) |
| 2 pyrimidyl | Br | 42% | — |

The following $R_5X$ are contemplated to be useful in preparing phenols of the invention.

| $R_5$ | X |
|---|---|
| 3 pyrimidyl | bromo |
| 3 pyridyl | bromo |
| 4 pyridyl | bromo |
| 3 pyrazyl | bromo |
| 2 fluorophenyl | bromo |
| 3 fluorophenyl | bromo |
| 4 fluorophenyl | bromo |
| 4 methoxyphenyl | bromo |

As well as other known bromo- and iodo-aromatic species.

Preparation of Example Compounds of Formula I

Example 1 a) Preparation of 3-[[3,5-dimethyl-4-[3-(5-methyl-2-furanyl)propyl]oxy]phenyl]-5-methyl-1,2,4-oxadiazole

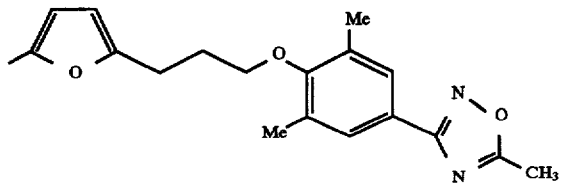

Diethyl azodicarboxylate (DEAD, 1.15 mL; 7.3 mmol) was added dropwise over a 3 min period to a solution of triphenylphosphine (1.91 g; 7.3 mmol), 3-(5-methyl-2-furanyl)propanol (see Ex. 9c) prepared according to the method of Intermediate 1 (1.2 g; 8.56 mmol), and 2,6-dimethyl-4-[3-(5-methyl) 1,2,4-oxadiazol)-yl]phenol (1.5 g; 7.3 mmol) prepared by the method of Intermediate 8, but substituting the appropriate starting materials therefor at room temperature under nitrogen (mild exotherm), cooled to room temperature, and was added to ethyl acetate/hexane. The precipitated triphenyl phosphate oxide (0.2 g) was removed by filtration. The filtrate was washed succesively with water (1x), dil. sodium hydroxide (2x50 mL), water (1x), and brine (1x50 mL), dried over anhydrous magnesium sulfate, and concentrated in vacuo to yield 5.3 g of a white solid. The solid product was chromatographed on silica gel while eluting with ethyl acetate/hexane (1:9). The appropriate fractions were concentrated in vacuo to afford 1.2 g (50%) of 2-methyl-5-[3-[2,6-dimethyl-4-(5-methyl-1, 2,4-oxadiazol-2-yl-phenoxy)]-propyl]-furan, as a clear colorless oil.

b) Preparation of 8[2,6-dimethyl-4-(5-methyl-1,2,4-oxadiazol-3-yl)phenoxy]oct-3-en-2,5-dione 0.71 (2.2 mmol) of 2-methyl-5-[3-[2,6-dimethyl-4-(5-methyl-1,2,4-oxadiazol-2-yl-phenoxy)propyl]-furan in 8 mL of ethanol was added to 0.68 g (1.1 mmol) of magnesium monoperoxyphthalate (MMPP) at room temperature under nitrogen with stirring and allowed to stir for 3 hours. The mixture was then allowed to stand overnight. An additional MMPP (0.14 g) was added to the mixture and then dilute sodium bicarbonate solution was added. The reaction mixture was extracted with methylene chloride (2x), the organic layer was dried ($MgSO_4$) and concentrated in vacuo to afford 0.664 g of the title compound which was used in the next step without further purification.

c) Preparation of 3-[[3,5-dimethyl-4-[3-(6-methyl-3-pyridazinyl)propyl]oxy]phenyl]-5-methyl-1,2,4-oxadiazole

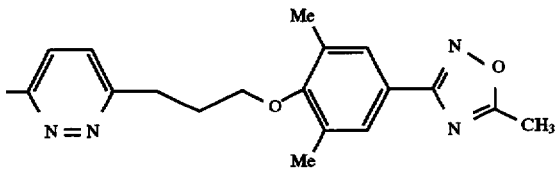

Hydrazine hydrate (0.060 mL; 1.94 mmol) was added to a solution of 0.664 g (1.94 mmol) of 6-[2-[2,6-dimethyl-4-(5-methyl-1,2,4-oxadiazol-2-yl-phenoxy)]-ethyl]-hex-3-en-2,4-dione in methanol. Water and methylene chloride were added to the reaction mixture. The organic layer was separated, dried over anhydrous magnesium sulfate, filtered, and the filtrate was concentrated in vacuo to yield a yellow oil, which crystallized. The product was passed through silica gel eluting with ethyl acetate/hexane (4:6) and then gradiated to 100% ethyl acetate. The resulting product was rechromatographed on the silica gel eluting with ethyl acetate to afford 436 mg (66%) of a compound of formula I (Formula I; $R_1$, $R_2$=3,5-dimethyl, $R_{3-6}$-methyl, $R_4$=hydrogen, $R_5$=5-methyl- 1,2,4-oxadiazol-3-yl, Y=1,3 propylene), as a yellow solid, m.p. 106°–107.5° C.

Example 2 a) Preparation of 4-[3,5-dimethyl-4-[3-(2-furanyl)propyl]oxy]benzonitrile

Potassium iodide (1.43 g; 8.6 mmol) was added to a mixture of 2-(3-chloropropyl)-furan (Intermediate 2) (11.1 g; 76.8 mmol) from preparation 4 in 100 mL of NMP, and the reaction mixture was allowed to react for 10 min. To the above mixture was added 2,6-dimethyl-4-cyanophenol (11.29 g; 76.71 mmol) and potassium carbonate (11.79 g; 85.3 mmol), and the reaction mixture was warmed. Cooled to room temperature, turned into ice $K_2CO_3$ extracted with EtOAc (4x200 mL), the combined organics were washed with $H_2O$ (2x100 mL), dried over MgSo and filtered and concentrated in vaccuo and purified by chromatography on MPLC eluting with 5% ethyl acetate/hexane, 15.56 g (79%) of 2-[3-(2,6-dimethyl-4-cyanophenoxy)-propyl]furan, as a clear oil, was obtained.

b) Preparation of N-hydroxy-3,5-dimethyl-4[[3-(2-furanyl)propyl]oxy]benzenecarboximidamide

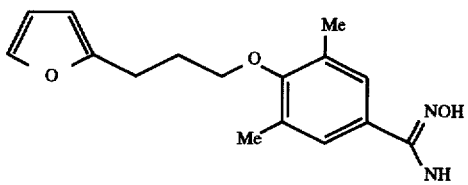

To a solution of 4.997 g (19.57 mmol) of 4-[3,5-dimethyl-4-[3-(2-furanyl)propyl]oxy]benzonitrile in 120 mL of ethanol was added at room temperature potassium carbonate (13.43 g; 97.17 mmol) and 6.92 g (79.58 mmol) of hydroxylamine hydrochloride and the mixture was stirred for 70 h at room temperature. The reaction mixture was filtered, the filtrate concentrated in vacuo, the residue was dissolved in ethyl acetate, and the organic layer was washed with water (2×25 mL) and dried over anhydrous magnesium sulfate The ethyl acetate solution was concentrated in vacuo to yield 6.0 g of a crystalline product which upon recrystallization from methylene chloride/hexane afforded 5.07 g (89.9%) of N-hydroxy-3,5-dimethyl-4[[3-(2-furanyl)propyl]oxy] benzenecarboximidamide, as a crystalline solid, m.p. 100.5°–101° C.

c) Preparation of 3-[[3,5-dimethyl-4-[3(2-furanyl)propyl] oxy]phenyl]-5-methyl-1,2,4-oxadiazole

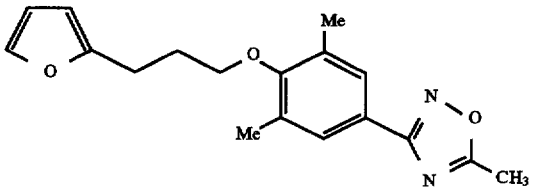

Pyridine (15 mL) was added at room temperature to 1.19 g (4.15 mmol) of N-hydroxy-3,5-dimethyl-4[[3-(2-furanyl) propyl]oxy]benzenecarboxyimidamide and then 0.45 mL of acetyl chloride was added slowly (slightly exothermic) to the above mixture. The resulting mixture was refluxed for 4 h. The above reaction mixture was poured into water, the aqueous mixture was extracted with ethyl acetate (5×50 mL), the combined organic layers were washed with water (4×50 mL), brine (50 mL), dried over anhydrous magnesium sulfate and concentrated in vacuo. The brown oil was purified by chromatography on MPLC eluting with 10% ethyl acetate/hexane to afford 0.759 g (59%) of 3-[[3,5-dimethyl-4-[3(2-furanyl)propyl]oxy]phenyl]-5-methyl-1,2,4-oxadiazole (Formula II; $R_3$==$R_4$=hydrogen, $R_1R_2$=3,5-dimethyl, Y=1,3-propylene, $R_5$=5-methyl-1,2,4-oxadiazolyl), as a crystalline solid, m.p. 44°–45° C. It is contemplated that a compound of formula I is prepared by the method of Example 1b and 1c.

d) Preparation of 4-[3,5-dimethyl-4-[3-(3-pyridazinyl) propyl]oxy]benzonitrile

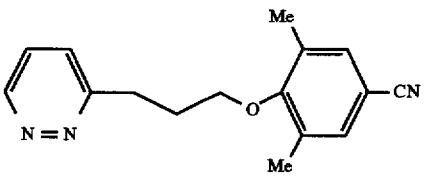

To a solution of 3-[[3,5-dimethyl-4-[3(2-furanyl)propyl] oxy]phenyl]-5-methyl-1,2,4-oxadiazole (2.18 g; 8.93 mmol) from 2a (above) in 60 mL of acetone at room temperature was added 17 mL of 0.05M dimethyldioxirane in acetone, and the mixture was stirred at room temperature for 2.5 h. The mixture was concentrated in vacuo, the residue was dissolved in methylene chloride under nitrogen at room temperature with stirring, and 0.35 mL 85% hydrazine hydrate was added to the methylene chloride solution. The desired product was isolated by the procedure of Example 8e and purified by chromatography (2×) on MPLC eluting with ethyl acetate then 90% ethylacetate/hexane followed by 70% ethyl acetate/hexane to afford 1.069 g of 4-[3,5-dimethyl-4-[3-(3-pyridazinyl)propyl]oxy]benzonitrile.

e) Preparation of N-hydroxy-3,5-dimethyl-4-[[3-(3-pyridazinyl]propyl]oxy]benzenecarboximidamide

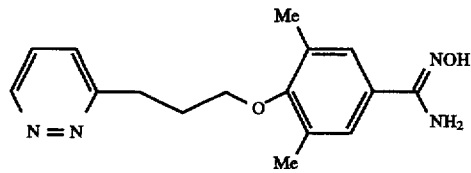

To a solution of 4-[3,5-dimethyl-4-[3-(3-pyridazinyl) propyl]oxy]benzonitrile (1.069 g; 3.99 mmol) in 25 mL of ethanol was added 2.76 g (19.97 mmol) of potassium carbonate followed by 1.39 g hydroxylamine hydrochloride (20 mmol) at room temperature and the mixture was stirred for 2.5 days. The reaction mixture was filtered, the filtrate concentrated in vacuo, and the residue collected was dissolved in 100 mL of water. Sodium chloride was added to the aqueous solution, and the resulting aqueous layer was extracted with ethyl acetate (5×100 mL). The organic layer was dried over MgSO$_4$, filtered, and the filtrate was concentrated in vacuo to afford 0.745 g (62%) of N-hydroxy-3,5-dimethyl- 4-[[3-(3-pyridazinyl]propyl]oxy] benzenecarboximidamide, as a white solid.

f) Preparation of 5-difluoromethyl-3-[[3,5-dimethyl-4-[3-(3-pyridazinyl)propyl]oxy]phenyl]-1,2,4-oxadiazole

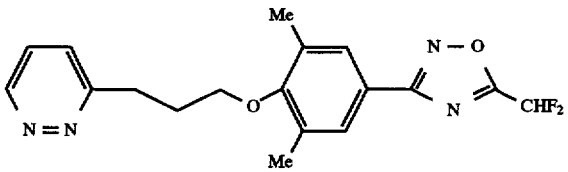

A mixture of 0.745 g (2.48 mmol) of 4-[3,5-dimethyl-4-[3-(3-pyridazinyl)propyl]oxy]benzonitrile and 0.8 mL (8.0 mmol) of ethyl difluoroacetate in 8 mL of NMP was heated to 100° C. under nitrogen with stirring for 4 days. The mixture was poured into 200 mL of water, and the aqueous solution was extracted with ethyl acetate(5×100 mL). The combined organic layer was washed with water (2×100 mL) and brine (1×100 mL), dried (over MgSO₄), and concentrated in vacuo to yield a clear oil. The oil was purified by chromatography on MPLC eluting with 60% ethyl acetate/hexane to afford 0.255 g (29%) of 5-difluoromethyl-3-[[3, 5-dimethyl-4-[3-(3-pyridazinyl)propyl]oxy]phenyl]-1,2,4-oxadiazole. (Formula I; $R_1$, $R_2$=3,5-dimethyl, $R_3$=$R_4$-hydrogen, $R_5$=5-difluoromethyl-1,2,4-oxadiazol-3-yl, Y=1,3 propylene). Recrystallization from ether yields a crystalline solid, m.p. 94°–95° C.

g) Preparation of 5-trifluoromethyl-3-[[3,5-dimethyl-4-[3-(3-pyridazinyl)propyl]oxy]phenyl]-1,2,4-oxadiazole

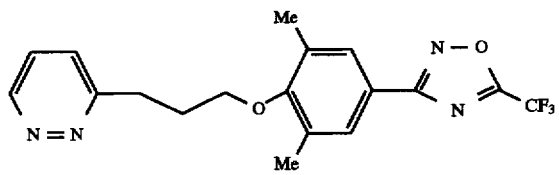

A mixture of 0.654 g (2.18 mmol) of the compound of Example 2e, above, 0.45 mL of ethyl trifluoroacetate, and 0.66 g (4.78 mmol) of potassium carbonate in 8 mL of NMP was heated to 100° C. under nitrogen with stirring for 24 hrs. The mixture was poured into 500 mL of water, and the aqueous solution was extracted with ethyl acetate (5×100 mL). The combined organic layer was washed with water (5×100 mL) and brine (1×100 mL), dried (over MgSO₄), and concentrated in vacuo. The residue was purified by chromatography on MPLC eluting with 80% ethyl acetate/hexane to afford a compound of formula I, $R_3$=$R_4$=hydrogen, $R_1$, $R_2$=3,5-dimethyl, $R_5$=5-trifluoromethyl-1,2,4-oxadiazol-3-yl, Y=1,3 propylene, as a crystalline solid, m.p. 50.5°–51.5° C.

Example 3 a) Preparation of 5-[3-[2,6-dimethyl-4-[3-(5-methyl-1,2,4-oxadiazolyl)]phenoxy]propyl]-2-furancarboxaldehyde

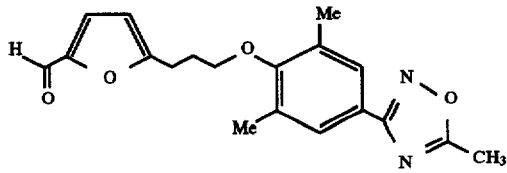

A solution of the compound prepared in example 2C, (0.84 g; 2.69 mmol) dissolved in 10 mL of DMF (dried over molecular sieves) with stirring under nitrogen was chilled in an ice-bath and 0.5 mL (5.38 mmol) of phosphorus oxychloride was added dropwise and the resulting reaction mixture was stirred for 30 min, and then the ice bath was removed. The reaction mixture was diluted with 100 mL of water, basified (to pH 10) with 2N sodium hydroxide solution, and the solid that formed was filtered, and dried to yield 0.85 g of yellow solid. Recrystallization from ether, after treatment with charcoal, yielded a bright yellow solid, 0.58 g (63%) of a compound of formula II, (Formula II; $R_3$=5-formyl, $R_4$=hydrogen, $R_1$,$R_2$=3,5-dimethyl, $R_5$=5-methyl-1,2,4-oxadiazol-3-yl, Y=1,3-propylene) (OGL-2298-88; WIN 68774), m.p. 68°–69° C. It is contemplated that by blocking the carbonyl and then using the methods of Example 1b and 1c, then deblocking, the corresponding compound of formula I is obtained.

b) Preparation of 5-difluoromethyl-2-[3-[2,6-dimethyl-4-(5-methyl-1,2,4-oxadiazol-3-yl)phenoxy]-propyl]-furan

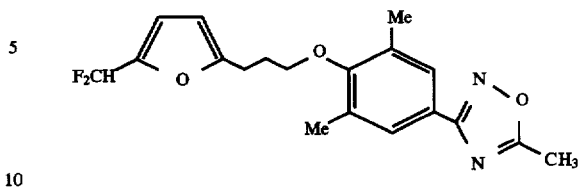

The compound prepared in example 3a (1.74 g; 5.11 mmol) and 3 mL of diethylaminosulfur trifluoride (DAST) were combined at room temperatuare with stirring under argon. After stirring 5 days at room temperature, the above solution was diluted with methylene chloride and the mixture was slowly poured onto ice. The organic layer was separated, washed with water (1×) and brine (1×), decolorized with charcoal, dried over magnesium sulfate, and concentrated in vacuo to yield a brown oil. The brown oil was chromatographed on silica gel column eluting with 10% hexane/methylene chloride and then methylene chloride to afford 1.17 g (63%) of a compound of Formula II; $R_4$=hydrogen; $R_3$=5-difluoromethyl, $R_1$,$R_2$=3,5-dimethyl; Y=1,3-propylene, $R_5$=5-methyl-1,2,4-oxadiazolyl, as a viscous yellow oil, which upon recrystallization from methanol, yielded off-white needles, m.p.38°–39° C.

c) Preparation of

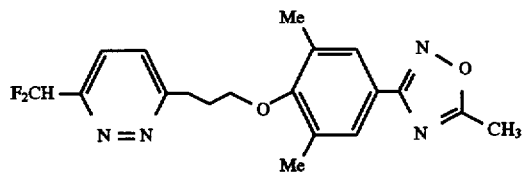

The compound prepared in example 3b (0.92 g; 2.54 mmol) was dissolved in 30 mL of acetone under argon at room temperature with stirring. To the above solution, 30 mL (2.7 mmol) of dimethyldioxirane (0.09M) in acetone, chilled to −80° C., was added in one portion. Additional dimethyldioxirane (0.09M) in acetone (2×10 mL) was added, the reaction mixture was stirred at room temperature for 1.5 days, and the mixture was concentrated in vacuo at 40° C. The residue was dissolved in 10 mL of methylene chloride under nitrogen at room temperature with stirring, and 0.3 mL (8.2 mmol) of 85% hydrazine hydrate was added to the methylene chloride solution. The reaction mixture was diluted with methylene chloride and shaken with water. The mixture was filtered, the organic layer was washed with water (1×), brine (1×), dried over magnesium sulfate, and concentrated in vacuo to afford 0.74 g of a viscous yellow oil. Chromatography on silica gel eluting with 60% hexane/ethyl acetate yielded 80 mg (8%) of a compound of formula I, (Formula I; $R_4$=6-difluoromethyl, $R_3$=hydrogen, $R_1$, $R_2$=3,5-dimethyl, Y-1,3 propylene, $R_5$=5-methyl-1,2,4-oxadiazol-3-yl) a yellow oil that crystallized on standing.

Example 4 a) 5-propyl-2-furancarboxaldehyde

To a solution of 13.04 g (0.118 mol) of 2-propylfuran in 800 mL of ether cooled at 0° C. with stirring under nitrogen was added dropwise 52 mL (0.130 mol) of 2.5M n-butyllithium. The reaction mixture was allowed to warm to room temperature and then refluxed for 40 min. The reaction mixture was cooled to −60° C., 10.1 mL (0.130 mol) of DMF in 10 mL of ether was added, and the resulting mixture was stirred at −60° C. for 45 min, and warmed to room temperature. The above mixture was quenched with 10 mL of saturated aqueous ammonium chloride, diluted with water to form a clear aqueous layer, and the organic layer was washed with water, and brine. The organic layer was dried over anhydrous magnesium sulfate, treated with a small amount of a charcoal, filtered, and concentrated to yield 13.95 g of a crude oil. The kughelrohr distillation of this oil (75°–105° C.) afforded 10.5 g (64.5%) of 5-propyl-2-furancarboxaldehyde.

b) Methyl 3-(5-propyl-2-furanyl)prop-2-enoate

To a solution of trimethylphosphonoacetate (12.34 g ; 61.6 mmol) in 500 mL of THF cooled to −78° C. under nitrogen with stirring, 136 mL (61.6 mmol) of 0.5M potassium bis(trimethylsilyl)amide was added dropwise over a ½ h period. The reaction mixture was stirred continuously at −78° C. for 1 hr. To the mixture was added 8.5 g (61.6 mmol) of 5-propyl-2-furancarboxaldehyde and 3 mL of THF over a 10 min period with stirring. After 1 h, stirring was stopped and the reaction mixture was allowed to warm to room temperature over a 2 h period. The reaction mixture was quenched with an aqueous solution of saturated ammonium chloride with stirring, and water was added to dissolve the precipitated salts into solution. The THF/agueous solution was washed with ether (200 mL), and the aqueous layer was washed again with 100 mL of ether. The combined organic layer was washed with brine, dried over anhydrous magnesium sulfate, filtered, and concentrated in vacuo to yield 10.95 g (87.9%) of methyl 3-(5-propyl-2-furanyl)prop-2-enoate.

c) Methyl 3-(5-propyl-2-furanyl)propionate

A solution of the compound from (b) above, (12.57 g, 64.5 mmol) in ethanol (200 mL) was added to a suspension of 500 mg of 5% palladium on carbon in 100 mL of ethanol, and the mixture was placed on a Paar hydrogenator and hydrogenated with $H_2$. Palladium on carbon was filtered off by passing the reaction mixture through Super-Cel™ (filter agent) and the residue was washed with ethanol. The filtrate was concentrated in vacuo to yield 13 g of an oil. After the Kughelrohr distillation, the oil (40°–75° C.) was purified-bypassing through flash silica column (hexane, 20% ether/hexane) followed by MPLC chromatography (5% ethyl acetate/hexane) to yield 6.5 g (51.4%) of methyl 3-(5-propyl-2-furanyl)propionate.

d) 3-(5-propyl-2-(furan)propan-1-ol

To a mixture of 1.25 g (33 mmol) of LAH in THF under nitrogen with stirring at 0° C., 6 g (31 mmol) of methyl 3-(5-propyl-2-furyl)propionate in THF was added dropwise, and the mixture was warmed to room temperature and stirred overnight. The reaction mixture was quenched with 1.25 mL of water, 1.25 mL of 15% sodium hydroxide solution, and 3.75 mL (×3) of water. The white mixture was filtered to remove the solid, and water, ether, and ethyl acetate were added to the flitrate. The organic layer was separated, dried over magnesium sulfate and concentrated in vacuo, and the residue was passed through a dry flash silica column to afford 4.63 g (88.8%) of the desired product.

e) 5-Propyl-2-[3-[2,6-dimethyl-4-(2-methyl-tetrazol-5-yl)phenoxy]-propyl]furan

Diethyl azodicarboxylate (DEAD, 3.88 g; 22.3 mmol) was added under nitrogen to a stirred and cooled (−10° C.) solution of triphenylphosphine (5.84 g; 22.3 mmol), of the compound prepared in d, above, (3.75 g; 22.3 mmol), and Intermediate 8 (5 g; 24.5 mmol) and the mixture was stirred for 20 min. Water and methylene chloride (25 mL) were added to the mixture and the layers were separated. The organic layer was washed with 2N NaOH solution (2×), HCl solution, brine, dried over magnesium sulfate, and concentrated in vacuo to yield a white solid (13 g). The white solid was purified by a large dry flash silica column (hexane, 30% and 70% ethyl acetate/hexane) followed by a medium size MPLC column chromatography (15% and 30% ethyl acetate/hexane) to afford 6.64 g (84%) of a compound of formula II, (Formula II; $R_1$, $R_2$=3,5-dimethyl, $R_3$=hydrogen, $R_4$=5-n-propyl, $R_5$=2-methyltetrazol-5-yl), m.p. 38°–39° C.

Example 5 a) Preparation of 2-ethyl-5-[3-(2,6-dimethyl-4-cyanophenoxy)-propyl]furan

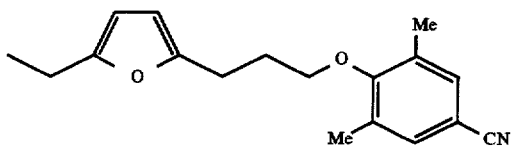

Diethyl azodicarboxylate (DEAD, 12 g; 69 mmol) was added to a solution of triphenylphosphine (18 g; 69 mmol), 2-ethyl-4-(3-hydroxypropyl)furan (Intermediate I) (10.7 g; 69 mmol), and 4-cyano-2,6-dimethylphenol (11.2 g; 76 mmol) in 150 mL of methylene chloride at 10° C. The mixture was stirred for 10 min. The reaction mixture was then allowed to stand at room temperature overnight. Solids were removed by filtration. Water was added to the filtrate, layers were separated, the organic layer was washed with dilute sodium hydroxide solution and brine (2×100 mL), dried over anydrous magnesium sulfate, filtered, and the filtrate was concentrated in vacuo to yield a brown solid (40 g). The brown solid was passed through a silica gel eluting first with ethyl acetate/hexane (1:9) and followed by ethyl acetate/hexane (4:6). The appropriate fraction was concentrated in vacuo to afford 20 g of the product which was chromatographed (3×) through a medium size MPLC column eluting with 5% ethyl acetate/hexane (1st), 5% ethyl acetate/hexane (2nd), and hexane (3rd) followed by 5% ethyl acetate/hexane, respectively, to afford 9.2 g (42.7%) of 2-ethyl-5-[3-(2,6-dimethyl-4-cyanophenoxy)propyl]furan.

b) The cyano moiety is then elaborated to a suitably substituted 1,2,4-oxadiazolyl or 5-tetrazolyl moiety as in the preparation of Intermediates 7–8 and 5–6 respectively, giving a compound of formula II, wherein Y is 1,3-propylene, $R_1$, $R_2$ is 3,5-dimethyl, $R_3$ is ethyl, $R_4$ is hydrogen and $R_5$ is as described above.

c) Preparation of 3-ethyl-6-[3-(2,6-dimethyl-4-cyanophenoxy)-propyl]-pyridazine

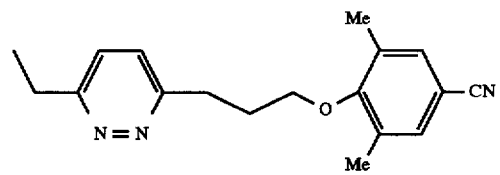

The magnesium salt of monoperoxyphthalic acid (MMPP, 2.9 g; 5.85 mmol) in 25 mL of water was added to a solution of 1.1 g (3.9 mmol) of the compound prepared in 5b above in 50 mL of ethanol at room temperature and under nitrogen with stirring. After 1 hr, 50 mL of dilute sodium bicarbonate solution and ether were added to the mixture. The ether layer was separated, washed with water and brine. Hydrazine hydrate (1.5 mL) was added to the ether solution. The ether layer was washed with brine, dried over anhydrous magnesium sulfate, filtered, and concentrated in vacuo. The residue was chromatographed (2×) on a small alumina column eluting with ethyl acetate to afford 0.352 g (30.6%) of the described product, as a yellow oil.

d) Preparation of 3-ethyl-6-[3-(2,6-dimethyl-4-aminohydroximinomethylphenoxy)-propyl-pyridazine

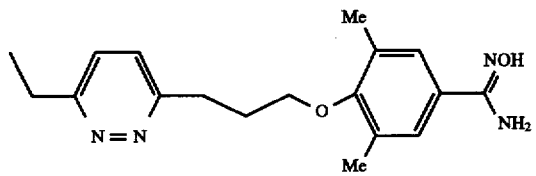

0.672 g (2.27 mmol) of the pyridazine prepared in 5c, above, 0.789 g (11.35 mmol) of hydroxylamine hydrochloride, 1.57 g (11.35 mmol) of potassium carbonate, and 25 mL of ethanol were combined at room temperature under nitrogen with stirring, and the mixture was warmed to reflux for 24 hr. The reaction mixture was allowed to stand overnight at room temperature. The next day it was filtered, and the filtrate was concentrated in vacuo to afford 0.66 g (88.6%) of 3-ethyl-6-[3-(2,6-dimethyl-4-hydroxyimideamide-phenoxy)-propyl]-pyridazine, as a yellow solid.

e) Preparation of 3-ethyl-6-[3-[2,6-dimethyl-4-(5-methyl-1,2,4-oxadiazol-2-yl-phenoxy)]-propyl]-pyridazine

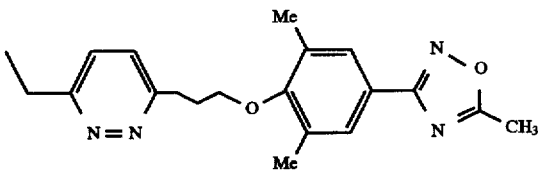

0.5 g (1.5 mmol) of hydroxyimideamide prepared in 5d above, 0.207 g (1.5 mmol) of potassium carbonate were combined in 10 mL of N-methylpyrrolidine (NMP) at room temperature and under nitrogen with stirring. 0.11 mL (1.5 mmol) of acetyl chloride was added to the reaction mixture (the brown suspension became yellow and solids went into solution). The mixture was (slowly) heated to 100°–105° C. where it remained for 45 min, cooled to room temperature, and water was added to the mixture. The resulting suspension was filtered, the filtrate was washed with ether (2×50 mL), and the combined organic layers were washed with ice-water (3×50 mL) and brine (1×50 mL). The organic layer was dried over anhydrous magnesium sulfate, filtered, and concentrated in vacuo to afford a brown oil. The brown oil was chromatographed on a small MPLC column to yield 0.23 g of clear oil which was rechromatographed on a neutral alumina column eluting with hexane/ethyl acetate (8:2) to afford a colorless oil (0.22 g). This oil was crystallized from warm ether/pentane to yield 120 mg of 3-ethyl-6-[3-[2,6-dimethyl-4-(5-methyl-1,2,4-oxadiazol-2-yl-phenoxy)]-propyl]-pyridazine (Formula I; $R_1$, $R_2$=3,5-dimethyl, $R_3$=hydrogen, $R_4$=6-ethyl, $R_5$=5-methyl-1,2,4-oxadiazol-3-yl), as colorless needles, m.p. 72°–75° C.

f) The N-oxide of 5e was by exposing Example 5e to MCPBA; m.p. 135°–136° C.

Example 6 a) Preparation of 2-methyl-5-[3-(2,6-dimethyl-4-cyanophenoxy)-propyl)furan

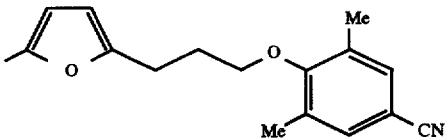

Diethyl azodicarboxylate (DEAD, 11.9 mL; 75.6 mmol) was added dropwise over a 10 min period to a solution of triphenylphosphine (19.8 g; 75.6 mmol), (2-methyl-5-furanyl)propanol (ex 1a, 9c and 12a) (10.6 g; 75.6 mmol), and 4-hydroxy-3,5-dimethyl-benzonitrile (12.2 g; 83.2 mmol) in methylene chloride cooled in an ice-bath under nitrogen with stirring. After 10 min, a solid formed. Additional methylene chloride (50 mL) was added to the mixture and the resulting suspension was filtered. The filtrate was washed with water (2×100 mL) and brine (1×100 mL). The organic layer was dried over anhydrous magnesium sulfate, and concentrated in vacuo to yield a brown oil which crystallized on standing. The solid product was chromatographed on silica gel eluting with ethyl acetate/hexane (2:8), and the appropriate fractions were concentrated in vacuo to afford 16.43 g (81%) of 2-methyl-5-[3-(2,6-dimethyl-4-cyanophenoxy)-propyl)furan. The cyano moiety is then elaborated to a suitably substituted 5-tetrazolyl moiety as in the preparation of Intermediates 5–6 or oxadiazolyl as in Intermediates 7–8, giving a compound of formula II wherein $R_3$ is methyl, $R_4$ is hydrogen, $R_1$, $R_2$ is 3,5-dimethyl Y is 1,3-propylene and $R_5$ is as described.

b) Preparation of 3-methyl-6-[3-(2,6-dimethyl-4-cyanophenoxy)-propyl)-pyridazine

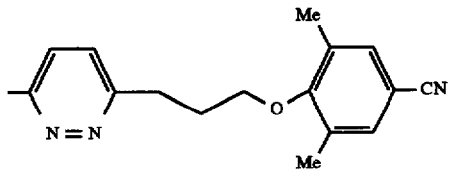

The compound prepared in 6a (9.6 g; 35.6 mmol) in 125 mL of ethanol was added to MMPP (26.38 g; 53.4 mmol) in 75 mL of water at room temperature under nitrogen with stirring. After 1 hr, dilute sodium bicarbonate solution was added and the mixture was stirred for 1 hr. The reaction mixture was extracted with ether (2×250 mL), organic layer was separated, and 7 mL of hydrazine (aqueous) was added to the ether solution. The organic layer was washed with brine (1×100 mL), dried over anhydrous magnesium sulfate and concentrated in vacuo to yield a yellow oil. The oil was chromatographed on silica gel eluting with ethyl acetate/ hexane (3:7) first and then gradiating to 100% ethyl acetate. The appropriate fractions were concentrated in vacuo to afford 6.55 g (65.5%) of 3-methyl-6-[3-(2,6-dimethyl-4-cyanophenoxy)propyl)pyridazine.

c) Preparation of 3-methyl-6-[3-(2,6-dimethyl-4-aminohydroxyiminomethyl-phenoxy)-propyl]pyridazine

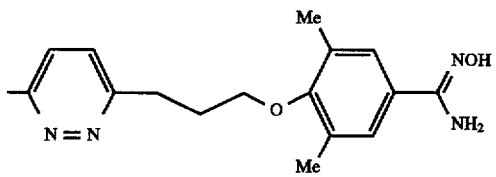

A mixture of 3-methyl-6-[3-(2,6-dimethyl-4-cyanophenoxy)propyl]pyridazine from example 6b (1.21 g; 4.3 mmol), 1.49 g (21.5 mmol) of hydroxylamine hydrochloride, and 2.97 g (21.5 mmol) of potassium carbonate in ethanol was stirred at room temperature for 10 days. The reaction mixture was filtered, and the filtrate was concentrated in vacuo to afford 0.57 g (43%) of 3-methyl-6-[3-(2,6-dimethyl-4-aminohydroxyiminomethyl-phenoxy)-propyl]pyridazine, as a yellow solid.

d) Preparation of 3-methyl-6-[3-[2,6-dimethyl-4-(5-difluoromethyl-1,2,4-oxadiazol-2-yl-phenoxy)]-propyl]pyridazine

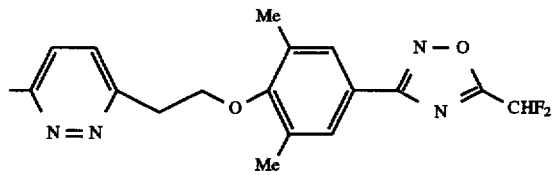

A mixture of 0.60 g (1.91 mmol) of 3-methyl-6-[3-(2,6-dimethyl-4-amino-hydroxyiminomethyl-phenoxy)propyl]pyridazine from example 6c and 0.57 mL (5.73 mmol) of ethyl difluoroacetate in 7 mL of NMP was briefly heated to 120° C., and then heated at 100° C. for 2.5 days. Upon cooling ether and water were added to the mixture and the layers were separated. The aqueous layer was extracted with ether (2×30 mL). The combined organic layers were washed with cold water (1×50 mL) and brine (1×50 mL), respectively, and dried over anhydrous magnesium sulfate and concentrated in vacuo to yield a yellow oil (120 mg.;16.8%). This oil was combined with a previous sample prepared by the same method and purified by TLC preparative plate eluting with ethyl acetate to afford 171 mg of a yellow oil which crystallized on standing. This solid was chromatographed on MPLC small column eluting with ethyl acetate to afford 151 mg of a compound of formula I wherein $R_1$, $R_2$=3,5-dimethyl, $R_4$=hydrogen, $R_3$=6-methyl, $R_5$=5-difluoromethyl-1,2,4-oxadiazol-3-yl, Y=1,3-propylene, as a light yellow solid, m.p. 102.5°–103° C.

Example 7 a) Preparation of 4-[3,5-dimethyl-4-[3-(5-furanyl-2-furanyl)propyl]oxy]benzonitrile

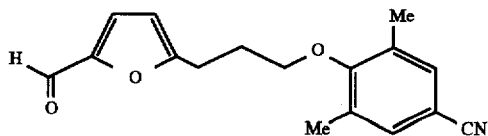

To a stirred solution of 4.43 g (17 mmol) of 2-[3-(2,6-dimethyl-4-cyanophenoxy)-propyl]furan, prepared in example 2a in dry DMF cooled to 0° C. under nitrogen was slowly added 3.3 mL (35 mmol) of phosphorus oxychloride dropwise, and the reaction mixture was stirred at 0° C. for 30 min and then was allowed to warm to room temperature. After standing overnight the reaction mixture was poured into 400 mL of water, 10% NaOH solution was added in portions until the pH was 9.0, and the mixture was stirred for 30 min. A yellow solid formed was filtered and dried to afford 444.65 g (95%) of 4-[3,5-dimethyl-4-[3-(5-furanyl-2-furanyl)propyl]oxy]benzonitrile. The yellow solid was recrystallized from methanol to afford 3.97 g of the nitrile, m.p. 61°–62° C. The compound can be protected and the cyano moiety elaborated to a suitably substituted 1,2,4-oxadiazole or 5-tetrazolyl moiety as in the preparation of Intermediates 7–8 or 5–6, respectively, giving a compound of formula II, which can be further elaborated to a compound of formula I using the method of Example 1b and 1c.

b) Preparation of 5-hydroxymethyl-2-[3-(2,6-dimethyl-4-cyanophenoxy)-propyl]-furan

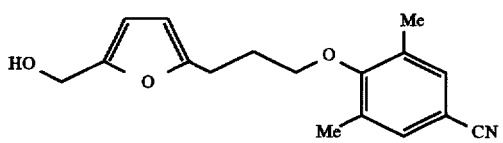

5-:Formyl-2-[3-(2,6-dimethyl-4-cyanophenoxy)-propyl]-furan from example 7a (21.69 g; 76 mmol) was dissolved in 200 mL of methanol/THF (1:1) with stirring under nitrogen, and the solution was chilled in an ice-water bath for 30 min and 2.88 g (76 mmol) of sodium borohydride was added in one portion. The resulting mixture was stirred in the ice-water bath. The mixture was quenched with 10% NaOH solution after 10 min and allowed to stand overnight. The reaction mixture was concentrated in vacuo and the residue was partitioned between methylene chloride and water. The organic layer was washed with water (1×) and brine (1×), dried over magnesium sulfate, filtered through Super-Cel™, and the filtrate was concentrated in vacuo to yield 20.96 g of an orange oil. The residue was chromatographed on silica gel, eluting with 5–6% ethyl acetate/methylene chloride to afford 11.32 g (52%) of 5-hydroxymethyl-2-[3-(2,6-dimethyl-4-cyanophenoxy)-propyl]-furan, as a viscous oil which crystallized on standing; m.p. 37°–38° C. The alcohol is protected, then the 4-cyano moiety is then elaborated to a suitably substituted 1,2,4-oxadiazolyl or 5-tetrazolyl moiety as in the preparation of Intermediates 7–8 or 5–6, respectively, giving a compound of formula II, which can be further elaborated to the corresponding compound of formula I.

c) Preparation of 5-methoxymethyl-2-[3-(2,6-dimethyl-4-cyanophenoxy)-propyl]-furan

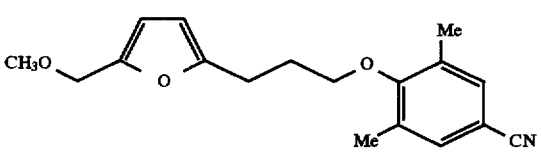

A solution of 5-hydroxymethyl-2-[3-(2,6-dimethyl-4-cyanophenoxy)-propyl]-furan from example 7b (0.44 g: 1.54 mmol) in 5 mL of dioxane with stirring under nitrogen was heated to 40° C., and 0.28 g (5 mmol) of crushed KOH was added. To the above reaction mixture dimethylsulfate (0.15 mL; 1.59 mmol) was added dropwise with stirring. After 1 hr. additional dimethylsulfate (0.15 mL) was added to the mixture, and the reaction mixture was allowed to react at 40° C. for 2 h and then at room temperature overnight. The mixture was filtered through Super-Cel™, the residue was washed with methylene chloride, the filtrate was washed with water (1×) and brine (1×), and dried over magnesium sulfate. The solvent was concentrated in vacuo to yield 0.48 g of a yellow oil which was purified by chromatography on silica gel eluting with a gradient of 20%, 10%, and 0% hexane/methylene chloride to afford 0.4 g (87%) of 5-methoxymethyl-2-[3-(2,6-dimethyl-4-cyanophenoxy)-propyl]-furan, as a clear viscous oil. The cyano moiety can be elaborated to a suitably substituted 1,2,4-oxadiazolyl or 5-tetrazolyl moiety as in the preparation of Intermediates 7–8 or 5–6, respectively, giving a compound of formula II.

d) Preparation of 5-Methoxymethyl-2-[3-(2,6-dimethyl-4-cyanophenoxy)-propyl]-furan; (4.23 g prepared as in 1c) was dissolved in 50 mL of acetone under nitrogen with stirring at room temperature, and 100 mL (1.35 mmol) of chilled (to −78° C.) dimethyldioxirane (0.09M) in acetone was added to the above solution and the reaction mixture was allowed to stir at room temperature for 16 h. The mixture was concentrated in vacuo to yield, 0.75 g of a viscous yellow oil.

e) Preparation of 3-methoxymethyl-6-[3-(2,6-dimethyl-4-cyanophenoxy)-propyl]-pyridazine

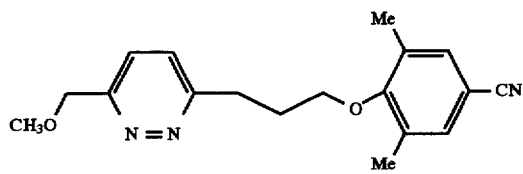

The compound from example 7d was dissolved in 25 mL of methylene chloride at room temperature under nitrogen with stirring, and 1 mL of 85% hydrazine hydrate was added. The resulting yellow solution was stirred for 30 min and then was allowed to stand at room temperature overnight. The reaction mixture was diluted with methylene chloride, the organic layer was washed with water (4×50 mL) and brine (1×50 mL), dried over MGSO$_4$, and concentrated in vacuo to yield 0.33 g of a viscous orange oil. The orange oil was purified by chromatography on silica gel eluting with ethyl acetate to afford 750 mg of 3-methoxymethyl-6-[3-(2,6-dimethyl-4-cyanophenoxy) propyl]-pyridazine, as an orange viscous oil.

f) Preparation of 3-methorymethyl-6-[3-(2,6-dimethyl-4-aminohydroximino-methylphenoxy)-propyl]-pyridazine

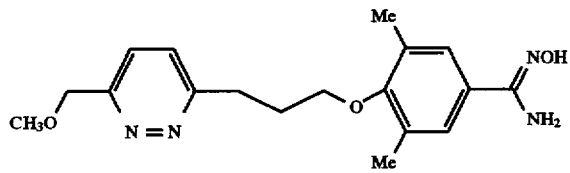

3-Methoxymethyl-6-[3-(2,6-dimethyl-4-cyanophenoxy) propyl]-pyridazine from example 7e (750 mg; 2.4 mmol), hydroxylamine hydrochloride (830 mg; 12 mmol), potassium carbonate (1.66 g; 12 mmol), and 20 mL of ethanol were combined at room stmperature under nitrogen with stirring. The reaction mixture was allowed to stir for 24 h at room temperature, diluted with ethyl acetate, filtered, and the solid residue was washed with ethyl acetate. The combined organic layer was concentrated in vacuo to afford 720 mg (87%) of 3-methoxymethyl6-[3-(2,6-dimethyl-4-aminohydroximino-methylphenoxy)-propyl]pyridazine, as a yellow solid.

g) Preparation of 3-methoxymethyl-6-[3-[2,6-dimethyl-4-(5-difluoromethyl-1,2,4-oxadiazol-2-yl-phenoxy)]-propyl] pyridazine

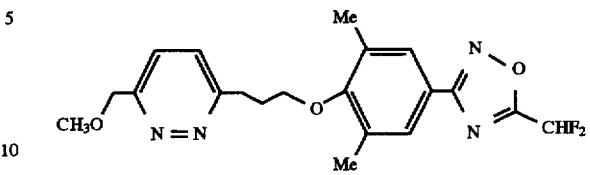

The compound prepared in example 7f (720 mg; 2.09 mmol) was dissolved in 10 mL of dry N-methylpyrrolidinone with stirring under nitrogen, and 0.63 mL (6.27 mmol) of ethyl difluoroacetate was added in one portion and the resulting mixture was heated at 100° C. for 3.5 days. The brown solution was diluted with brine, extracted with ether, and the aqueous layer and the organic layer were separated. The ether solution was washed with water (1×) and brine (1×), dried over MgSO$_4$, and concentrated in vacuo to yield 0.24 g of an oil. The aqueous layer was extracted with methylene chloride (1×), and the organic layer was washed with water (1×) and brine (1×). The methylene chloride solution was dried (MgSO$_4$) and concentrated in vacuo to yield 0.13 g of an oil. The combined product was purified by chromatography on MPLC eluting wiith hexane/ethyl acetate (4:96) to afford 77 mg (9%) of a compound of formula I, 3-methoxymethyl-6-[3-[2,6-dimethyl-4-(5-difluoromethyl-1,2,4-oxadiazol-2-yl) phenoxy]-propyl]-pyridazine, (Formula I; $R_1$, $R_2$=3,5-dimethyl, $R_3$=hydrogen, $R_4$=6-methoxymethyl, $R_5$=5-difluoromethyl-1,2,4-oxadiazolyl, y=1,3-propylene) as a solid, m.p. 79°–81° C. (after drying in vacuo).

Example 8 a) Preparation of 5-(2-methyl-1,3-dioxolan-2-yl)-2-[3-(2,6-dimethyl-4-cyanophenoxy)-propyl]furan.

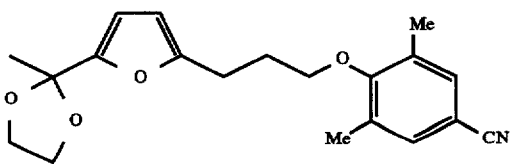

To a mixture of 5-(2-methyl-1,3-dioxolan-2-yl)-2-(3-chloropropyl)-furan (7.0 g; 30.34 mmol) (Intermediate 3b) and potassium iodide (0.506 g; 3.04 mmol) in NMP heated to 50° C., was added potassium carbonate (4.71 g; 34.08 mmol) and 2,6-dimethyl-4-cyanophenol (4.62 g; 31.39 mmol) and the reaction mixture was allowed to react at 50° C. for 4 days. The reaction mixture was then cooled to room temperature poured into water (160 mL) and extracted with ethyl acetate, washed with water twice, then brine, then dried over magnesium sulfate and concentrated in vacuo. The product was further purified by chromatography on MPLC eluting with 12% ethyl acetate/hexane 6.87 g (74%) of 5-(2-methyl-1,3-dioxolan-2-yl)-2-[3-(2,6-dimethyl-4-cyanophenoxy)-propyl]furan, as a clear oil was obtained. The cyano moiety is then elaborated to a suitably substituted 1,2,4-oxadiazolyl or 5-tetrazolyl moiety as in the preparation of Intermediates 7–8 or 5–6, respectively, giving a compound of formula II or can be used in the next step.

b) Preparation of 6-(2-methyl-1,3-dioxolan-2-yl)-3-[3-(2,6-dimethyl-4-cyanophenoxy)-propyl]-pyridazine

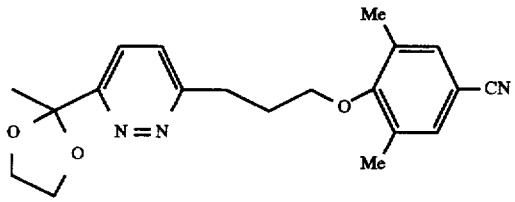

Following a procedure similar to that described in Example 3c, 5-(2-methyl-1,3-dioxolan-2-yl)-2-[3-(2,6-dimethyl-4-cyanophenoxy)-propyl]furan; (1.05 g; 3.08 mmol), 48 mL (0.06M) of dimethyldioxirane in acetone, and 10 mL of acetone were reacted. The resulting product was disolved in methanol and reacted with 85% hydrazine hydrate (0.15 mL; 4.49 mmol) then purified by chromatography on silica gel with 65% ethyl acetate/hexane to afford 0.511 g (47%) of 6-(2-methyl-1,3-dioxolan-2-yl)-3-[3-(2,6-dimethyl-4-cyanophenoxy)propyl]-pyridazine.

c) Preparation of 6-(2-methyl-1,3-dioxolan-2-yl)-3-[3-(2,6-dimethyl-4-hydroxyimideamidephenoxy)-propyl]pyridazine

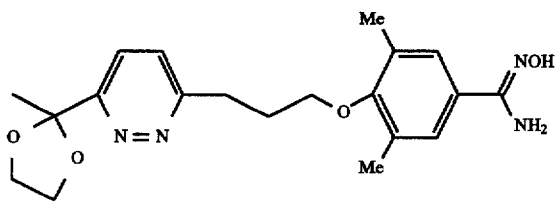

To a solution of the compound prepared in example 8c, 6-(2-methyl-1,3-dioxolan-2-yl)-3-[3-(2,6-dimethyl-4-cyanophenyxy)-propyl]-pyridazine (0.511 g; 1.45 mmol) in 9 mL of ethanol was aded potassium carbonate (1.09 g; 7.05 mmol) and hydroxylamine hydrochloride (4.90 mg; 12 mmol). The reaction mixture was allowed to stir overnight at room temperature, concentrated in vacuo, and the residue was dissolved in 50 mL of water. The aqueous solution was extracted with ethyl acetate (4×50 mL), and the combined organic layer was washed with water (1×50 mL) and brine (1×50 mL), and dried over MgSO$_4$. The organic layer was concentrated in vacuo to afford 502 mg (89.6%) of 6-(2-methyl-1,3-doxolan-2-yl)-3-[3-(2,6-dimethyl-4-aminohydroximinomethylphenoxy)-propyl]-pyridaxine, as a white solid.

d) Preparation of 6-(2-methyl-1,3-dioxolan-2-yl)-3-[3-[2,6-dimethyl-4-(5-difluoromethyl-1,2,4-oxadiazol-2-yl-phenoxy)]-propyl]-pyridazine

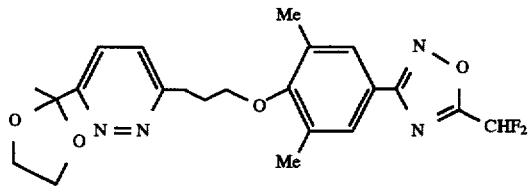

Following a procedure similar to that described in Example 2f, 6-(2-methyl-1,3-dioxolan-2-yl)-3-[3-(2,6-dimethyl-4-aminohydroximinomethylphenoxy)-propyl ]-pyridazine from example 8c (1.023 g; 2.65 mmol), 5 drops of dry N-methylpyrrolidine, and 5 mL of ethyl difluoroacetate were combined with stirring under nitrogen, and the resulting mixture was heated at 100° C. for 3 days. The mixture was concentrated in vacuo, the residue was dissolved in ethyl acetate, ethyl acetate solution was washed with water (5×50 mL) and brine (1×50 mL) and dried over MgSO$_4$. The organic solvent was concentrated in vacuo and the residue was purified by chromatography on MPLC eluting with 70% ethyl acetate/hexane and ethyl acetate to afford the desired product 6-(2-methyl-1,3-dioxolan-2-yl)-3-[3-[2,6-dimethyl-4-(5-difluoromethyl-1,2,4-oxadiazol-2-yl)-phenoxy]-propyl]-pyridazine.

e) Preparation of 6-acetyl-3-[3-[2,6-dimethyl-4-(5-difluoromethyl-1,2,4-oxadiazol-2-yl) -phenoxy]-propyl]-pyridazine

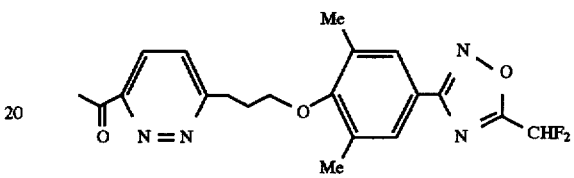

A mixture of 0.24 g (0.538 mmol) of 6-(2-methyl-1,3-dioxolan-2-yl)-3-[3-[2,6-dimethyl-4-(5-difluoromethyl-1,2,4-oxadiazol-2-yl)-phenoxy]-propyl]-pyridazine from example 8d, 20 mL of acetic acid, 5 mL of water, and 5 mL of 2M HCl solution was heated to reflux for 24 hr. The reaction mixture was added to a freshly prepared sodium bicarbonate solution, the aqueous layer was extracted with ethyl acetate (4×50 mL), and the combined organic layer was washed with water (50 mL) and brine (100 mL), dried and concentrated in vacuo. The residue was purified by chromatography on MPLC eluting with 30% ethyl acetate/hexane followed by recrystallization from ethyl acetate/hexane to afford 165 mg (76%) of 6-acetyl-3-[3-[2,6-dimethyl-4-(5-difluoromethyl-1,2,4-oxadiazol-2-yl) phenoxy]-propyl]-pyridazine (Formula I; $R_1$, $R_2$=3,5-dimethyl, $R_{3-6}$-acetyl, $R_4$=hydrogen, $R_5$=5-difluoromethyl-1,2,4-oxadiazolyl, Y=1,3-propylene), m.p. 95°–96° C.

f) Preparation of 6-(2-methyl-1,3-dioxolan-2-yl)-3-[3-[2,6-dimethyl-4-(5-trifluoromethyl-1,2,4-oxadiazol-2-yl) phenoxy]-propyl]-pyridazine

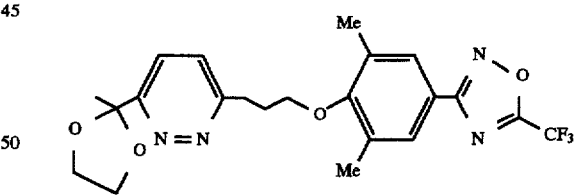

Following a procedure similar to that described in Example 8d, to a solution of 6-(2-methyl-1,3-dioxolan-2-yl)-3-[3-(2,6-dimethyl-4-aminohydroximino-methylphenoxy)propyl]-pyridazine (0.502 g; 1.3 mmol) dissolved in 8 mL of dry N-methylpyrrolidine was added 0.36 g (2.6 mmol) of potassium carbonate and 0.28 mL (1.98 mmol) of trifluoroacetic anhydride, and the mixture was heated to 70° C. One additional equivalent of trifluoroacetic anhydride was added and the mixture was heated to 70° C. The mixture was poured into 200 mL of water, the aqueous solution was extracted with ethyl acetate (5×50 mL), and the combined organic layer was dried and concentrated in vacuo to residue. The residue was taken up and was purified by chromatography on MPLC eluting with 50% ethyl acetate/hexane to afford 0.395 g (65%) of 6-(2-methyl-1,3-dioxolan-2-yl)-3-[3-[2,6-dimethyl-4-(5-trifluoromethyl-1,2,4-oxadiazol-2-yl-phenoxy)]-propyl]pyridazine.

g) Preparation of 6-acetyl-3-[3-[2,6-dimethyl-4-(5-trifluoromethyl-1,2,4-oxadiazol-2-yl)-phenoxy]-propyl]pyridazine

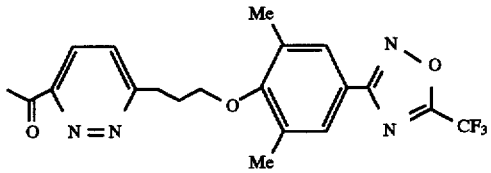

A mixture of 0.5 g (1.08 mmol) of 6-(2-methyl-1,3-dioxolan-2-yl)-3-[3-[2,6-dimethyl-4-(5-trifluoromethyl-1,2,4-oxadiazol-2-yl)-phenoxy]-propyl]-pyridazine from example 8f, 8 mL of acetic acid, and 2 mL of water was heated to reflux. After adding acid solution, the reaction mixture was refluxed for 5 h. Upon cooling, the above reaction mixture was added to a freshly prepared sodium bicarbonate solution with stirring. The product was isolated and purified by chromatography on MPLC eluting with 30–50% ethyl acetate/hexane and recrystallized from hexane to afford 0.30 g (66%) of 6-acetyl-3-[3-[2,6-dimethyl-4-(5-trifluoromethyl-1,2,4-oxadiazol-2-yl)-phenoxy]-propyl]-pyridazine ($R_1$, $R_2$=3,5-dimethyl, $R_3$=6-acetyl, $R_4$=hydrogen, $R_5$=5-trifluoromethyl-1,2,4-oxadiazolyl, Y=1,3-propylene), as a crystalline solid, m.p. 86°–87° C.

h) Preparation of 6-(1,1-difluoro-ethyl)-3-[3-[2,6-dimethyl-4-(5-trifluoromethyl-1,2,4-oxadiazol-2-yl)-phenoxy]-propyl]-pyridazine

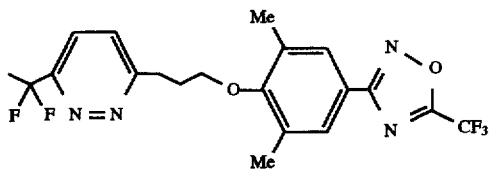

To a mixture of 220 mg (0.523 mmol) of 6-acetyl-3-[3-[2,6-dimethyl-4-(5-trifluoromethyl-1,2,4-oxadiasol-2-yl)-phenoxy]-propyl]-pyridazine (from Example 8g) in 2 mL of methylene chloride was added 0.1 mL of diethylaminosulfur trifluoride (DAST) and the mixture was left at room temperature for 3 days. Additional DAST was added (1.0 mL) and the mixture heated to reflux then left at room temperature for 2 days. Finally DAST (4 mL) were added and the mixture heated to reflux until starting material was not evident by TLC. The product was purified by chromatography on MPLC eluting with 30% ethyl acetate/hexane to afford 6-(1,1-difluoroethyl)-3-[3-[2,6-dimethyl-4-(5-trifluoromethyl-1,2,4-oxadiazol-2-yl)phenoxy]-propyl]-pyridazine (Formula I; $R_1$, $R_2$=3,5-dimethyl, $R_3$=6–1,1-difluoroethyl, Y=1,3-propylene, $R_4$=hydrogen, $R_5$=5-trifluoromethyl-1,2,4-oxadiazolyl), as a crystalline solid, m.p. 54.5° C.

i) Using the methods described above, for reacting DAST with a carbonyl of compound I, and the compound of example 8e as a substrate compound of formula I was obtained wherein $R_1$, $R_2$ are 3, 5 dimethyl, $R_3$=6–1,1 difluoroethyl, $R_4$ is H, Y is 1,3-propylene and $R_5$ is 5-difluoromethyl-1,2,4-oxadiazol-3-yl, m.p. 73.5°–74° C.

Example 9 a) Methyl β-(5-methyl-2-furanyl)-propenoate

To a solution of trimethylphosphonoacetate (13.09 mL; 66 mmol) in 500 mL of THF cooled to –78° C. under nitrogen with stirring, 132 mL (61.6 mmol) of 0.5M potassium bis(trimethylsilyl)amide in toluene was added dropwise over a ½ h period. The reaction mixture was stirred continuously at –78° C. for 1 hr. To the mixture was added 6.66 g (66 mmol) of 5-methyl-2-furanyl-2-carboxaldehyde and 3 mL of THF over a 10 min period with stirring. After 1 h, stirring was stopped and the reaction mixture was allowed to warm to room temperature over a 2 h period. The reaction mixture was quenched with an aqueous solution of saturated ammonium chloride with stirring, and water was added to dissolve the precipitated salts into solution. The THF/agueous solution was washed with ether (200 mL), and the aqueous layer was washed again with 100 mL of ether. The combined organic layer was washed with brine, dried over anhydrous magnesium sulfate, filtered, and concentrated in vacuo and distilled (130°–135° C./16 mm) to yield 8 g (87.9%) of the desired product.

b) Methyl 3-(5-methyl-2-furanyl)propionate A mixture of ethyl β-(5-methyl-2-furanyl)acrylate (8 g) in methanol (200 mL) and 1.5 g of 5% palladium on carbon was placed on a Paar hydrogenator and hydrogenated with $H_2$- Palladium on carbon was filtered off by passing the reaction mixture through Super-Cel™ (filter agent) and the residue was washed with ethanol. The filtrate was concentrated in vacuo to yield 8 g of methyl 3-(5-methyl-2-furanyl)propionate.

c) 3-(5-methyl-2-furanyl)propanol (Example 1a, 6a and 12a)

To a solution of ethyl 3-(5-methyl-2-furanyl)propionate (3.6 g, 20 mmol) in 50 mL of THF at 0° C. was added dropwlse under nitrogen 8 mL of diisobutylaluminum hydride (1M in hexane), and the mixture was stirred at room temperature over-night. The resulting solution was diluted with 2 mL of water in 10 mL of THF and brine, and the mixture was stirred for 30 min. The solid was removed by filtration, and the filtrate was diluted with 20 mL of water, extracted with methylene chloride. The orgaic layer was washed with water, dried over magnesium sulfate, and concentrated in vacuo. The residue was purified by passing through MPLC column (ethyl acetate/hexane) to afford 1.11 g of the desired product.

d) 5-methyl-2-[3-[2,6-dimethyl-4-(2-methyl-tetrazol-5-yl)phenoxy]-propyl]furan

Diethyl azodicarboxylate (DEAD, 1.4 g in 20 mL of THF) was added dropwise under nitrogen to a stirred and cooled (–10° C.) solution of triphenylphosphine (2.09 g), 3-(5-methyl-2-(propanol)furanyl) (1.11 g; 8 mmol), and 4-(2-methyl-tetrazol-5-yl)-2,6-dimethylphenol (1.632 g; 8 mmol) in 50 mL of THF and the mixture was stirred for 20 min. The mixture was diluted with 200 mL of water, extracted with ether (3×50 mL), and the organic layer was washed with water (3×25 mL), 10% NaOH solution, and water. The organic layer was dried over magnesium sulfate, and concentrated in vacuo to yield an oil which was passed through MPLC column (ethyl acetate/hexane 3:7) to afford 1.75 g (67.1%) of 5-methyl-2-[3-[2,6-dimethyl- 4-(2-methyl-tetrazol-5-yl)phenoxy]-propyl]furan (Formula II; $R_3$=5-methyl, $R_1$,$R_2$=3,5-dimethyl $R_4$=hydrogen, Y=1,3-propylene, $R_5$=2-methyltetrazol-5-yl).

e) 5-Methyl-2-[3-[2,6-dimethyl-4-(2-methyl-tetrazol-5-yl)phenoxy]-propyl]-2,5 dimethoxy-2,5-dihydrofuran Sodium carbonate (1.2 g) was added to a cooled (–10° C.) solution of 5-methyl 2-[3-[2,6-dimethyl-4-(2-methyltetrazol-5-yl)phenoxy]-propyl]furan from example 9d (780 mg, 2.4 mmol) in 18 mL of methanol with stirring, and then bromine (0.135 g, 14 mmol) in 8 mL of methanol was added dropwise until the brown color persisted, and the resulting reaction mixture was allowed to stir at −10° C. for 45 min. To the mixture was added brine, extracted with ether (3×25 mL), and the organic layer was washed with water, dried over magnesium sulfate, and concentrated in vacuo to yield an oil which was purified by MPLC chromatography (ethyl acetate/hexane 3:7) to afford 820 mg (76.3%) of 5-methyl-2-[3-[2,6-dimethyl-4-]2-methyl-tetrazol-5-yl)phenoxy]-propyl]-2,5-dimethoxy-2,5-dihydrofuran.

f) 3-Methyl-6-[3-[2,6-dimethyl-4-(2-methyl-tetrazol-5-yl)-phenoxy]-propyl]-pyridazine Under nitrogen with stirring 5-methyl-2-[3-[2,6-dimethyl-4-(2-methyl-tetrazol-5-yl)phenoxy]-propyl]-2,5-dimethoxy-2,5-dihydrofuran (820 mg, 1.8 mmol), 0.8 mL of methanol, and 1.5 mL of 1% aqueous acetic acid solution were combined at room temperature, refluxed for 10 min, and then cooled to room temperature. To the above solution was added hydrazine hydrate (0.26 mL) over a 2 min period, and the mixture was allowed to reflux for 1 h, and cooled to room temperature. The mixture was diluted with water, the aqueous layer was extracted with methylene chloride, and the organic layer was washed with brine, dried over magnesium sulfate, and concentrated in vacuo to afford 180 mg (29%) of 3-methyl-6-[3-[2,6-dimethyl-4-(2-methyl-tetrazol-5-yl)-phenoxy]-propyl]-pyridazine (Formula I; $R_1$, $R_2$=3,5-dimethyl, $R_3$=6-methyl, $R_4$=hydrogen, $R_5$=2-methyltetrazol-5-yl), m.p. 114°–115° C.

Example 10 a) 5-Ethyl-2-[3-[2,6-dimethyl-4-(2-methyl-tetrazol-5-yl)phenoxy]-propyl]furan

Diethyl azodicarboxylate (DEAD, 4.84 g; 27.8 mmol) was added under nitrogen to a stirred and cooled (−20° C.) solution of triphenylphosphine (7.37 g; 27.8 mmol), 5-ethyl-2-(3-hydroxypropyl)furan (Intermediate 1c) (3.9 g; 25.3 mmol), and 4-(2-methyl-tetrazol-5-yl)-2,6-dimethylphenol (5.69 g; 27.8 mmol). The mixture was stirred at −20° C. for ½ h, and then was allowed to warm to room temperature overnight. Water (50 mL) was added to the mixture and the layers were separated. The aqueous layer was extracted with ether (3×50 mL), the organic layer was washed with 10% NaOH solution (3×50 mL), water, and dried over magnesium sulfate. The solvent was concentrated in vacuo to yield a residue and purified by MPLC column chromatography (ethyl acetate/hexane, 3:7) to afford 5.63 g (65%) of 5-ethyl-2-[3-[2,6-dimethyl-4-(2-methyl-tetrazol-5-yl)phenoxy] propyl]furan (Formula II; $R_3$=5-ethyl, $R_4$=hydrogen, $R_1$,$R_2$= 3,5-dimethyl, $R_5$=2-methyltetrazol-5-yl, Y=1,3-propylene).

b) The compound prepared in 9e was transformed into a compound of formula I by the method of Example 1b and 1c. ($R_3$=6-ethyl, Y=($CH_2$)$_3$, $R_1$, $R_2$=3,5-dimethyl, $R_4$=hydrogen, $R_5$=2-methyltetrazol-5-yl).

Example 11 a) 5-Propyl-2-[3-[2,6-dimethyl-4-(2-methyl-tetrazol-5-yl)phenoxy]-propyl]furan

Diethyl azodicarboxylate (DEAD, 3.88 g; 22.3 mmol) was added under nitrogen to a stirred and cooled (−10° C.) solution of triphenylphosphine (5.84 g; 22.3 mmol), 3-(5-propyl-2-(furanyl)propanol (Intermediate 4c) (3.75 g; 22.3 mmol), and 4-(2-methyl-tetrazol-5-yl)-2,6-dimethylphenol (5 g; 24.5 mmol) and the mixture was stirred for 20 min. Water and methylene chloride (25 mL) were added to the mixture and the layers were separated. The organic layer was washed with 2N NaOH solution (2×), HCl solution, brine, dried over magnesium sulfate, and concentrated in vacuo to yield a white solid (13 g). The white solid was purified by a large dry flash silica column (hexane, 30% and 70% ethyl acetate/hexane) followedby a medium size MPLC column chromatography (15% and 30% ethyl acetate/hexane) to afford 6.64 g (84%) of 5-propyl-2-[3-[2,6-dimethyl-4-(2-methyl-tetrazol-5-yl)phenoxy]-propyl]furan (Formula II; $R_1$, $R_2$=3,5-dimethyl, Y=1,3-propylene, $R_3$=5-propyl, $R_4$=hydrogen, $R_5$=2-methytetrazol-5-yl), m.p. 38°–39° C.

b) 1-Propyl-4-[3-[2,6-dimethyl-4-(2-methyl-tetrazol-5-yl-phenoxy)]-propyl]but-2-en-1,4-dione Sodium carbonate (6.32 g, 60 mmol) was added to a cooled (−10° C.) solution of 5-propyl-2-[3-[2,6-dimethyl-4-(2-methyl-tetrazol-5-yl) phenoxy]-propyl]furan (4.46 g, 13 mmol) in 35 mL of methanol with stirring, and then bromine (2.23 g, 14 mmol) in 10 mL of methanol was added dropwise, and the resulting reaction mixture was allowed to stir at −10° C. for 45 min. To the mixture was added brine and water, and the mixture was extracted with ether (3×), the organic layer was washed with brine, dried over magnesium sulfate, and conentrated in vacuo to yield 4.74 g of a yellow oil. The oil was purified by a large dry flash silica column (2×) chromatography (hexane, 30% ethyl acetate/hexane) to afford 1-propyl-4-[3-[2,6-dimethyl-4-(2-methyl-tetrazol-5-yl-phenoxy)]-propyl] but -2-en-1,4-dione as a 2nd fraction and 5-propyl-2-[3-[2,6-dimethyl-4-(2-methyl-tetrazol-5-yl)phenoxy]-propyl]-2,5-dimethoxy-2,5-dihydrofuran, as a first fraction.

c) 3-Propyl-6-[3-[2,6-dimethyl-4-(2-methyl-tetrazol-5-yl)-phenoxy]-propyl]-pyridazine Under nitrogen with stirring 1-propyl-4-[3-[2,6-dimethyl-4-(2-methyl-tetrazol-5-yl-phenoxy)]-propyl]but-2-en-1,4-dione (1.42 g, 3.8 mmol), 1.42 mL of methanol, and 2.63 mL of 1% aqueous acetic acid solution were combined at room temperature, refluxed for 10 min, and then cooled to room temperature. To the above solution was added hydrazine hydrate (0.29 mL; 9.5 mmol) over a 2 min period, and the mixture was allowed to reflux for 1 h, and cooled to room temperature. The mixture was diluted with water, the aqueous layer was extracted with methylene chloride (3×), and the organic layer was washed with brine, dried over magnesium sulfate, and concentrated in vacuo to afford 1.4 g of a yellow oil. The oil was passed through a silica column eluting with ethyl acetate/hexane (1:1) to afford 0.25 g (17.98%) of 3-propyl-6-[3-[2,6-dimethyl-4-(2-methyl-tetrazol-5-yl)phenoxy]-propyl]-pyridazine (Formula I; $R_1$, $R_2$=3,5-dimethyl, Y=1,3-propylene, $R_4$=hydrogen, $R_3$=6-propyl, $R_5$=2-methyltetrazol-5-yl), as a yellow oil. This oil was further purified by MPLC column chromatography and flurosil column chromatography (ethyl acetate/hexane) to yield a clear oil which crystallized, m.p.78°–80° C.

Example 12

Using the protocols described above, and the appropriate intermediates the following compounds of formula I were prepared.

FORMULA I

| Ex | R3, R4 Pyridazyl | R1 | R2 | Y = | R5 | M.P. |
|---|---|---|---|---|---|---|
| a | 6-propyl-3-pyridazyl | 3,5-dimethyl | | (CH2)3 | 5-CHF2-1,2,4-oxadiazolyl | 124–125 |
| b | 6-propyl-3-pyridazyl | 3-CH3 | H | (CH2)3 | 5-CHF2-1,2,4-oxadiazolyl | 131.5–136.5 |
| c | 6-ethyl-3-pyridazyl | 3,5-dimethyl | | (CH2)3 | 5-CHF2-1,2,4-oxadiazolyl | 82.5–83.5 |
| d | 6-ethyl-3-pyridazyl | 3-CH3 | H | (CH2)3 | 5-CHF2-1,2,4-oxadiazolyl | 85.5–86 |
| e | 6-ethyl-3-pyridazyl | H | H | (CH2)3 | 5-CF3-1,2,4-oxadiazolyl | 111.5–112 |
| f | 6-ethyl-3-pyridazyl | 3,5-dimethyl | | (CH2)3 | 5-CF3-1,2,4-oxadiazolyl | 60–60.5 |
| g | 6-methyl-3-pyridazyl | 3,5-dimethyl | | (CH2)3 | 5-CF3-1,2,4-oxadiazolyl | 68.5–70 |
| h | 6-methyl-3-pyridazyl | 3,5-dimethyl | | 1,3propylene | 5-CHF2-1,2,4-oxadiazolyl | 67.5–69 |
| i | 6-methyl-3-pyridazyl | 3-CH3 | H | 1,5pentylene | 5-CHF2-1,2,4-oxadiazolyl | 70.8–72.3 |
| j | 6-propy,1-3-pyridazyl | 3,5-dimethyl | | 1,3propylene | 5-cyclopropyl 1,2,4-oxadiazolyl | — |
| k | 6-propy,1-3-pyridazyl | 3-CH3 | H | 1,3propylene | 5-cyclopropyl 1,2,4-oxadiazolyl | 75.6–77.2 |
| l | 6-ethyl-3 pyridazyl | 3-CH3 | H | 1,3propylene | 5-CF3-1,2,4-oxadiazolyl | 91–91.5 |
| m | 6-ethyl-3 pyridazyl | H | H | 1,3propylene | 5-CF2H-1,2,4-oxadiazolyl | 90.5–91.5 |

Example 13 a) A slurry of 19 g of 2-acetyl furan (Aldrich), 57.8 g of aluminum chloride and 17.7 mL and bromine was heated to 65° C. for 2 hours. A resulting dark brown slurry was poured over ice and extracted with an ether. The organic phase was then washed twice with water and dried over potassium carbonate. Concentration of the organic phase provided 25 g of the dark brown oil. Distillation (0.5 mmHg 62° C. to 69° C.) provided 13.1 g. (28%) of a pale yellow oil which crystallized upon standing and was used without further purification.

b) To a solution of 13 g. of the product prepared in A above in 100 mL of 70% acetic acid, 3.6 g. of zinc powder was added slowly over 30 minutes. The mixture was filtered and concentrated in vacuo. The dark red mixture was diluted with ether and washed with water followed by sodium bicarbonate solution. The organic phase was dried over potassium carbonate and concentration of the organic phase provided 9 g. of the dark red oil. Crystallization from isopropyl acetate and hexanes provided 3.4 g. of a tan solid product melting point 57° C. to 59° C.

c) A solution of 3.4 g of 3-bromo 5-acetyl furan, 1.23 g of ethylene glycol and a catalytic amount of tosyl acid in 50 mL of benzene was refluxed under nitrogen with a Dean Stark Trap for 3 days. Upon cooling, the mixture was concentrated in vacuo, diluted with ether and washed with dil bicarbonate solution. The organic phase was dried over $K_2CO_3$. Concentration provided 4.2 g of the product as a viscous red liquid. Used without further purification (Quantitative).

d) To a solution of 4.2 g. of the product produced in B, C above in 100 mL of ether at −78° C. under nitrogen was added 1.9 mL of 10M n-butyl lithium. After 15 minutes the brown slurry was quenched with 4 g. of 3-chloro-1-iodopropane in 10 mL of HMPA. Upon warming to room temperature, the mixture was poured into water and washed four times. The organic phase was dried over potassium carbonate. Concentration of the organic phase provided 3.7 g. of crude product which was distilled (0.1 mmHg; 91°–95° C.) to provide 0.9 g. of the corresponding propylchloride product used without further purification.

e) A suspension of 1.2 g. of the phenol of Example 1a, 1.5 g. of the alkyl chloride prepared in 13d above, 0.4 g. of powdered potassium hydroxide and 0.9 g. of potassium iodide in 40 mLs of acetonitrile was refluxed under nitrogen for 20 hours. Filtration, concentration and flash filtration through kieselgel 60 with 2;1 hexane/EtOAc provided 3.7 g. of an orange oil which was subjected to MPLC affording 0.53 g. of the product as a yellow viscous oil.

f) To a solution of 0.53 g. of the dioxolane prepared in D above in 20 mL of acetone was added 0.1 g. of PPTs. The mixture was allowed to stir at room temperature for 14 hours, followed by reflux under nitrogen for 5 hours, concentration and extraction with ethyl acetate followed by a water wash and drying of the organic phase over potassium carbonate provided 0.48 g. of the product as a pale yellow viscous oil. Crystallization from isopropyl acetate and hexane provided 245 mg of the product as a tan powder, melting point 95° C. to 97° C., which can be reacted with MCPBA and hydrazine to prepare a compound of Formula I after the blocking of the acetyl moiety (Formula I $R_1$, $R_2$=3,5 dimethyl, $R_3$=6-acetyl, $R_4$=H, $R_5$=5-methyl-1,2,4-oxadiazolyl, Y=1,3 propylene) m.p. 99°–100.5° C.

Example 14

As further examples of the invention, the following anti-picornavirally effective 2-furanyl compounds of formula II can be elaborated to the corresponding pyridazines of formula I using the procedures previously described.

| Example | R1 | R2 | R3 | R4 | Y | R5 | M.P. |
|---|---|---|---|---|---|---|---|
| a | H | H | H | 5-acetyl | (CH2)5 | ethoxy-carbonyl | 85–87 |
| b | H | H | H | H | (CH2)5 | ethoxy-carbonyl | oil |
| c | H | H | H | H | (CH2)5 | ethoxy-carbonyl | 59–61 |
| d | | 3-bromo,H | H | 5-acetyl | (CH2)5 | 4,5-dihydro oxazole | 91–92 |
| e | | 3,5-dichloro | H | H | (CH2)5 | 4,5-dihydro oxazole | oil |
| f | | 3,5- | H | 5-acetyl | (CH2) | 2-methyl-5- | 77–78 |

-continued

| Example | $R_1$ | $R_2$ | $R_3$ | $R_4$ | Y | $R_5$ | M.P. |
|---|---|---|---|---|---|---|---|
| g | | 3,5-dimethyl | H | 5-(hydroxy)ethyl | 5 (CH$_2$) 5 | tetrazolyl 2-methyl-5-tetrazolyl | 92–94 |
| h | | 3,5-dimethyl | H | 5-formyl | (CH$_2$) 5 | 2-methyl-5-tetrazolyl | 63–65 |
| i | | 3,5-dimethyl | H | 5-hydroxy-methyl | (CH$_2$) 5 | 2-methyl-5-tetrazolyl | 74–75 |
| j | 3-bromo,H | | H | 5-propyl | (CH$_2$) 3 | phenyl | |
| k | 3-bromo,H | | H | H | (CH$_2$) 3 | phenyl | |
| l | | 3,5-dimethyl | H | 5-ethyl | (CH$_2$) 3 | 4-fluorophenyl | |

The following Examples of compounds of formula I were prepared by the method of 1b–c described above:

| 14m | 3-bromo,H | H | 6 propyl | (CH$_2$) 3 | phenyl | 102.6–103.1 |
|---|---|---|---|---|---|---|
| 14n | 3-bromo,H | H | H | (CH$_2$) 3 | phenyl | — | o. Using Example 145 in the method of 1b and 1c one obtains a compound of formula I wherein $R_1$=3-bromo, $R_2$, $R_4$=H, $R_3$=propyl, $R_5$=phenyl and Y=1,3 propylene.

p. Using the method of example 14o, example 141 was transformed to the corresponding compound of formula I, m.p. 114°–116° C.

Example 15 a. 0.5 g of 5-difluoromethyl-1,2,4-oxadiazol-3-yl-2,6-dimethyl-phenol was dissolved in 5 mls of THF and 0.11 g of propargyl alcohol and 0.81 g of triphenylphosphine was added. The reaction was cooled to 0° C. and DEAD (0.54 g) in 5 mls of THF was added slowly. The mixture was stirred and allowed to come to room temperature overnight. This mixture was absorbed onto silica gel and eluted using 2:1 hexane/EtOAc yielding 0.6 g of a yellow solid used without purification in the next step.

The product obtained above was taken up in 8 mL of triethylamine and combined with 0.53 g of 3-iodo-6-methoxypyridazine. To this mixture 14 mg of PdCl$_2$($\phi$3P)$_2$ and 11 mg of CuI was added. The mixture was allowed to stir at room temperature and the methoxy was allowed to stir at room temperature for 3 days. The mixture was filtered through Celite and absorbed onto silica gel eluted with a hexane/EtOAc mixture. The appropriate fractions were concentrated at a yield of 0.86 g or an amber oil that crystallized upon standing. Upon purification via MPLC 0.68 g of a compound of formula I wherein $R_3$ is methoxy, $R_4$=hydrogen, $R_5$ is 5-difluoromethyl-1,2,4-oxadiazol-3-yl, $R_1$, $R_2$ represent 3,5-dimethyl and Y is 1,3-propyl-1-yne.

b. 0.58 g of the compound described above was exposed to Lindlar catalyst in EtOAc to provide a compound of formula I wherein $R_3$ is methoxy, $R_4$ is hydrogen, $R_1$, $R_2$ represent 3,5-dimethyl, $R_5$ is 5-difluoromethyl-1,2,4-oxadiazol-3-yl and Y is 1,3-propylene, (m.p. 91°–93° C.)

c. Using the method of example 15a, but substituting a compound the appropriate materials of formula I was obtained; Y=1,3-propyl-1-yne, $R_1$, $R_2$=3,5-dimethyl, $R_3$=6-methoxy, $R_4$=H, $R_5$=5-trifluoromethyl-1,2,4-oxadiazol-3-yl, m.p. 110°–112° C.

d. Upon reduction as described in 15, one obtains the corresponding compound of formula 1 where Y=1,3-propylene, $R_1$, $R_2$=3,5-dimethyl, $R_3$=6-methoxy, $R_4$=H, $R_5$=5-trifluoromethyl-1,2,4-oxadiazol-3-yl, m.p. 59°–61° C.

Example 16 a. 3-(4-cyano-2,6-dimethylphenoxy)propionic acid (20.02 g) was combined with 45 mls of SOCl$_2$ in methylene chloride at room temperature and was allowed to stir overnight. Zn—Cu in 500 mL benzene, 39 mL DMA and 1.3 equiv. of ethyl-(3-iodo)propionate was heated to 69° C. for 3 hours, 1 equiv. of Pd[P$\phi_3$]$_4$ was added, after cooling 5 minutes, the acid chloride was added, and the mixture sat overnight. Upon workup ethyl(6-(4-cyano-2,6-dimethylphenoxy)-3-keto hexanoate is obtained in 80% yield, m.p. 45°–46° C.

b. 20.76 g of the product of 16a was taken up in 200 mL EtOH and 3.2 mL hydrazine was added. The mixture was then heated to reflux for 2 hours. Upon workup one obtains 6-(3-(4-cyano-2,6-dimethylphenoxy)propyl)-4,5-dihydropyridazin-3-one (93%), m.p. 124.5° C.

c. 5.713 g of the dihydro pyridazinone from 16b was taken up in 90 mL EtOAc and 1.4 mL Br$_2$ added. Upon workup 6-(3-(4-cyano-2,6-dimethylphenoxy)propyl)-3-hydroxypyridazine was obtained quantitative yield.

d. Using the method of example 6c and d a compound of formula I where $R_1$, $R_2$=3,5-dimethyl, $R_3$=6 hydroxy, $R_4$=H, $R_5$=5-difluoromethyl-1,2,4-oxadiazol-3-yl, Y=1,3-propylene was obtained.

e. The compound obtained in 16d was exposed to POCl$_3$ to afford a compound of formula I wherein $R_1$, $R_2$=3,5-dimethyl, $R_3$=6-chloro, $R_4$=H, $R_5$=5-difluoromethyl-1,2,4-oxadiazol-3-yl, Y=1,3-propylene, (87% yield), m.p. 100.5°–101.5° C.

f. The compound of 16d was exposed to POBr$_3$ yield a compound of formula I wherein $R_1$, $R_2$=3,5-dimethyl, $R_3$=6-bromo, $R_4$=H, $R_5$=5-difluoromethyl-1,2,4-oxadiazol-3-yl, Y=1,3-propylene, m.p. 91°–92° C.

g. 2.1 g of the compound of 16d was taken up in THF and 1.93 g of Lawesson's reagent added, the mixture was refluxed until starting material is no longer present. Upon workup a compound of formula I was obtained, $R_1$, $R_2$=3,5-dimethyl, $R_3$=6-thio, $R_4$=H, $R_5$=5-difluoromethyl-1,2,4-oxadiazol-3-yl, Y=1,3-propylene, m.p. 146°–148° C.

h. 200 mg of the compound of example 16 g was taken up in DMF and 80 mg CH$_3$I and 56 mg Et$_3$N added, and after 1 hour the mixture was worked up yielding a compound of formula I, $R_1$, $R_2$=3,5-dimethyl, $R_3$=6-methylthio, $R_4$=H, $R_5$=5-difluoromethyl-1,2,4-oxadiazol-3-yl, Y=1,3-propylene, (m.p. 98°–101° C.).

i. 32 g of the compound of 16 h was treated with 0.285 g of 50–60% MCPBA. Upon workup 0.167 g of a compound of formula I was obtained, $R_1$, $R_2$=3,5-dimethyl, $R_3$=6-methylsulfinyl, $R_4$=H, $R_5$=5-difluoromethyl-1,2,4-oxadiazol-3-yl, Y=1,3-propylene, m.p. 87°–89° C.

j. The compound of 16c was transformed to a compound of formula I by the method of example 6c and then 8f giving a compound of formula I (53%) ($R_1$, $R_2$=3,5-dimethyl, $R_3$=6-hydroxy, $R_4$=H, $R_5$=5-trifluoromethyl-1,2,4-oxadiazol-3-yl, Y=1,3-propylene.

k. The compound of 16 g was exposed to $POCl_3$ yielding (48%) of a compound of formula I. ($R_1$, $R_2$=3,5-dimethyl, $R_3$=6-chloro, $R_4$=H, $R_5$=5-trifluoromethyl-1,2,4-oxadiazol-3-yl, Y=1,3-propylene), m.p. 96°–98° C.

l. The compound of 16j was acetylated to give a compound wherein Y=1,3 propylene, $R_1$,$R_2$=3,5 dimethyl, $R_3$-acetoxy, $R_4$=H, $R_5$=5-methyl-1,2,4-oxadiazolyl, m.p. 69°–71° C.

Example 17 a. 130 mL of trifluoro acetic anhydride (chilled) was added to 50 g of 1-valine and allowed to warm to room temperature. The resulting material was vacuum distilled at 69°–71° C. giving 68.05 g of (81%) of 2-trifluoromethyl-2,5-dihydro-4-(1-methylethyl)-5-oxazalone.

b. 54.64 g of the oxazalone obtained in 17a was taken up in 150 mL of $CH_2Cl_2$, chilled and 50 mL of t-butylacrylate added followed by 50 mL $Et_3N$, dropwise. The reaction stirred overnight giving a yellow oil, yielding 95.9 g of the desired product 1,1-dimethylethyl 3-[2-(2-trifluoromethyl-2,5-dihydro-4-methylethyl-5-oxo-oxazolinyl)]propionate.

c. The product obtained above was taken up in 500 mL glacial acetic acid and 100.5 g of hydrazine hydrochloride added then the mixture was refluxed for 2 hours. Upon workup 6-trifluoro 4,5-dihydro-pyridazin-3-one was obtained in 59% yield. This product was treated with bromine in glacial acetic acid yielding 77.5%, 3-hydroxy-6-trifluoromethyl pyridazine. This product was exposed to $POBr_3$ giving 7.92 g 3-bromo-6-trifluoromethyl pyridazine.

d. The pyridazine above was reacted with propargyl alcohol (under Heck conditions), the product was then reacted with 4-cyano-3,5-dimethyl-phenol (according to the method of example 6a then reduced with palladium and carbon and elaborated to the 5-difluoromethyl, 1,2,4-oxadiazolyl species according to the method of 6c and d. To give a compound of formula I ($R_3$=$CF_3$, $R_4$=H, $R_1$, $R_2$=3,5-dimethyl, Y=1,3-propylene, $R_5$=5-difluoromethyl-1,2,4-oxadiazol-3-yl) m.p. 80°–81° C.

e. The following compound of formula I was prepared using the materials and methods described above. Each compound has the formula $R_3$=$CF_3$, $R_4$=H, $R_5$=5-methyl-1,2,4-oxadiazol-3-yl, Y=1,3-propylene, and $R_1$, $R_2$=3,5-dimethyl, m.p. 147°–148° C.

Example 18 a. 4-pentyne-1-ol was protected with t-butyldimethylsilychloride, the protected pentynol was reacted with 2-chloro-2-propen-1-ol under Heck Conditions. The resulting product was exposed to potassium t-butoxide in 18-crown-6 to yield 2-(3-(t-butyl dimethylsilyloxy)propyl)-4-methyl furan (15%). This product was then acid-deprotected.

b. 0.68 g of the furan alkanol and 0.88 g of 5-methyl-1,2,4-oxadiazol-3-yl was reacted under conditions of example 5, giving a compound of formula II in 67% yield.

c. The compound of example 18b was reacted with dimethyl dioxane and then hydrazine according to the method of example 3c to provide a compound of formula I wherein $R_1$, $R_2$=3,5-dimethyl, $R_3$=5-methyl, $R_4$=H, Y=1,3-propylene, $R_5$=5-methyl-1,2,4-oxadiazol-3-yl, m.p. 73°–74° C.

Example 19 a. To 42.1 g 3,6-dichloro pyridazine in acetone 10.5 g of NaI followed by 105 mL HI catalyst (Aldrich 21002-1) was added and left at room temperature for three days, upon workup a quantitative yield of 3,6-diiodopyridazine was obtained.

b. 5 g of 3,6-diiodopyridazine was dissolved in 30 mL DMSO with 0.6 g KF. The mixture was refluxed for 4 hours upon cooling. The mixture was taken up in $CHCl_3$, washed with water twice, then brine and dried over $MgSO_4$, and then concentrated in vacuo. The product was recrystallized from isopropylacetate giving 2.21 g (75%) of 3-iodo-6-fluoropyridazine.

c. 1.16 g of the product of 19b and 0.75 mL propargyl alcohol were reacted under Heck conditions (CuI, $PdCl_2$ $(P\phi_3)_2$, $Et_3N$) for 36 hours at room temperature. The product was absorbed onto silica, which was washed with hexane, then eluted with 1:1 EtOAc/hexane and used without purification in the next step.

d. 1.2 g of the alcohol obtained above was taken up in EtOAc and hydrogenated with Pd/carbon (0.5 g) under $H_2$. Solids were filtered off and the filtrate concentrated in vacuo to yield 3-(6-fluoro-3-pyridazyl)propanol.

e. 0.43 g of 4-(5-trifluoromethyl-1,2,4-oxadiazolyl) 2,6-dimethyl phenol in 10 mL THF was combined with 0.53 g triphenyl phosphine and 0.35 g of DEAD at −50° C., and the 0.26 g of the fluoropyridazinyl alkanol of 19d was added. Upon warming the mixture was absorbed on silica and eluted with 2:1 hexane/EtOAc, the crude product was then purified on MPLC yielding 200 mg of an oil that crystallized upon standing. The product was recrystallized from t-butylmethylether (m.p. 86°–87° C.) to give a compound of formula I; Y=1,3-propylene, $R_1$, $R_2$=3,5-dimethyl, $R_5$=5-trifluoromethyl-1,2,4-oxadiazol-3-yl, $R_4$=H, $R_3$=6-fluoro.

f. Using the method of 19e, the alcohol of 7d was reacted with 4-(5-difluoromethyl-1,2,4-oxadiazol-3-yl) 2,6-dimethylphenol to provide a compound of formula I wherein $R_1$, $R_2$=3,5-dimethyl, $R_3$=6-fluoro, $R_4$=H, Y=1,3-propylene, $R_5$=5-difluoromethyl-1,2,4-oxadiazol-3-yl; m.p. 92°–94° C.

g. 10.55 g of 3,6-dichloropyridazine was taken up in 100 mL $Et_3N$ and CuI (0.676 g), and $PdCl_2(P\phi_3)_2$ (2.5 g) added (Heck conditions). To this propargyl alcohol (4.2 mL) was added in 30 mL of $Et_3N$ upon work up 10.4 g of the chloropyridazyl alcohol was obtained.

h. 0.479 g of the unsaturated alcohol obtained in 19 g was reacted with 0.422 g of 4-hydroxy-3,5-dimethyl benzonitrile using the method of example 19e to provide 0.448 (53%) of the corresponding phenoxy ether. The product was transformed into a compound of formula I by the method of 2e and 2f; (formula I; $R_1$, $R_2$=3,5-dimethyl, $R_3$=6-chloro, $R_4$=H, Y=1,3-propyl-1-yne, $R_5$=5-trifluoromethyl-1,2,4-oxadiazol-3-yl), m.p. 118°–118.5° C. The acetylene linkage in Y can be reduced using Lindlar catalyst and the like to provide the corresponding compound of formula I wherein Y is 1,3-propylene.

i. Using the diiodo pyridazine of example 19A and the method of example 15A one obtains a compound of formula I wherein $R_1$, $R_2$=3,5-dimethyl, Y=1,3,-propylene, $R_3$=6-iodo, $R_4$=H, $R_5$=5-difluoromethyl-1,2,4-oxadiazol-3-yl, m.p. 113°–114.5° C.

Example 20 a. 2-acetyl 5-(3-(4-cyano-2,6,-dimethylphenoxy)propyl) furan was prepared from example 8A by deprotection of the carbonyl moiety. 21.42 g of this material was dissolved in 200 mL of 1:1 methanol/THF at 0° C., 2.88 g of $NaBH_4$ was added. After 5 minutes the reaction was quenched with 10% NaOH. Upon workup 11.32 g (52%) of the hydroxy ethyl compound is obtained.

b. 0.434 g of the compound of formula 20A was taken up in 4 mL acetone and was exposed to 26 mL dimethyl dioxyrane at room temperature forming the corresponding 2-hydroxy-5,6-dihydro-5-pyran-5-on-2-yl compound. (m.p. 104°–105° C., after workup).

c. 7.25 g of the compound as prepared in 20B was taken up in 66 mL of 1:1 $THF/H_2O$ and 27.60 mL hydrazine was added. The mixture was diluted with 200 mL $CH_2Cl_2$. The mixture was washed with water, then brine, dried over $MgSO_4$ and concentrated in vacuo, to an oil and used without further purification.

d. The 6-(1-hydroxyethyl)pyridazine formulation formed in 20c above was protected using diphenyl-t-butyl silylchloride. The product (an oil) was obtained in 99% yield.

e. Using the method of example 20D and finally deblocking the compound of formula I was obtained wherein $R_3$=1-hydroxyethyl, $R_1$, $R_2$=3,5-dimethyl, $R_4$=hydrogen, $R_5$=5-difluoromethyl-1,2,4-oxadiazol-3-yl and Y=1,3-propylene (71%).

f. 0.468 g of the compound of 20E was taken up in 20 mL $CH_2Cl_2$ and 0.16 mL DAST added. A compound of formula I was obtained ($R_3$=1-fluoroethyl, $R_4$=H, $R_1$, $R_2$=3,5-dimethyl, Y=1,3-propylene, $R_5$=5-difluoromethyl-1-1,2,4-oxadiazol-3-yl) m.p. 85° C. (66% yield).

g. 0.680 g of the compound of example 20F was exposed to 0.72 g of $MnO_2$ in EtOAc yielding the compound of example 8C; formula I ($R_1$, $R_2$=3,5-dimethyl, $R_3$=6-acetyl, $R_4$=H, Y=1,3-propylene, $R_5$=5-difluroromethyl-1,2,4-oxadiazol-3-yl); in quantitative yield.

h. Using 0.7 g of the compound of example 20G and exposing it to 2 equivalents of DAST as described in 7F, a compound of formula I wherein $R_1$, $R_2$ is 3,5-dimethyl, $R_3$=1,1-difluoromethyl, $R_4$=H, $R_5$=5-difluoromethyl-1,2,4-oxadiazol-3-yl, Y=1,3-propylene (68%), m.p. 73.5°–74° C.

Using the methods described herein the following compounds of formula I were prepared, wherein $R_1$, $R_2$=3,5-dimethyl, Y is 1,3-propylene, $R_4$ is H, $R_5$ is 5-$R^1$-1,2,4-oxadiazol-3-yl.

| Example | 6-$R_3$ | $R^1$ | M.P. | Yield |
|---|---|---|---|---|
| i | 1 fluoroethyl | $CH_3$ | 41–42__C. | 67% |
| j | acetyl | $CH_3$ | 99.5–100__C. | — |
| k | 1,1-difluoroethyl | $CH_3$ | 137–140__C. | 66% |
| l | 1 hydroxyethyl | $CF_3$ | 143__C. | — |
| m | 1 fluoroethyl | $CF_3$ | 48.5–50__C. | — |
| n | 1,1-difluoroethyl | $CF_3$ | 54–55__C. | — |

— = not recorded

Example 21 a. 7.5 g of the compound prepared in example 7B was treated with dimethyl dioxyrane as in example 20B, then hydrazine as in 20c yielded the corresponding hydroxy methyl pyridazine compound (77%) as an oil. The hydroxy methyl moiety was protected with pyran and the benzonitrile portion of the molecule elaborated to difluoromethyl-1,2,4-oxadiazol-3-yl using the method of example 7F and G to give, upon deprotection of the hydroxy methyl, a compound of formula I wherein $R_1$, $R_2$=3,5-dimethyl, $R_3$=6-hydroxymethyl, $R_4$=H, Y=1,3-propylene, $R_5$=5-difluoro-1,2,4-oxadiazol-3-yl, m.p. 120°–150° C.

b. The compound in 21A, when treated with $MnO_2$ according to example 20 g yields the compound of formula I wherein $R_1$, $R_2$=3,5-dimethyl, $R_3$=6-formyl, $R_4$=H, Y=1, 3-propylene, $R_5$=5-difluoro-1,2,4-oxadiazol-3-yl, m.p. 107–109.

c. The compound of 21B when treated with DAST according to example 21b yields a compound of formula I wherein $R_3$=6-difluoromethyl, $R_4$=H, Y=1,3-propylene, $R_5$=5-difluoro-1,2,4-oxadiazol-3-yl, m.p. 75°–76.3° C.

Using the methods described above, compounds of formula I were obtained wherein Y is 1,3-propylene, $R_1$, $R_2$ are 3,5-dimethyl, $R_4$ is hydrogen and $R_5$ is 5-$R^1$-1,2,4-oxadiazol-3-yl;

| Example | 6-$R_3$ | $R^1$ | M.P. |
|---|---|---|---|
| d | hydroxymethyl | propyl | 106–107__C. |
| e | formyl | propyl | 95–96__C. |
| f | methoxymethyl | $CF_3$ | 61–62__C. |
| g | methoxymethyl | $CH_3$ | 57–59__C. |
| h | $CF_2H$ | Ethyl | 125–129__C. |
| i | hydroxymethyl | $CF_3$ | 149–150__C. |

Example 22

As further examples, phenols described only generally thus far can be reacted with any known furan alkanol, furanyl alkyl halide or those described herein using the methods previously described herein to provide a compound of formula II, which can then be transformed into a compound of formula I. It is contemplated that any phenol disclosed in allowed application 07/869,287, incorporated herein by reference, is elaborated to a pyridazine of formula I, using the methods described above. For the reader's convenience the same nomenclature conventions described herein for compounds of formula I are adhered to, and a literature reference describing the known phenol is included.

| $R_1$ | $R_2$ | $R_5$ | Reference U.S. Pat. No. |
|---|---|---|---|
| H | H | 1,2,4-oxadiazol-2yl | 4,857,539 |
| H | H | 4,2-dimethyl-2-thiazolyl | 4,857,539 |
| H | H | 2-benzoxazolyl | 4,857,539 |
| 3,5-dichloro | | 3-furanyl | 4,857,539 |
| 3,5-dichloro | | 2-furanyl | 4,857,539 |
| 3,5-dichloro | | 2-thienyl | 4,857,539 |
| 3,5-dichloro | | 2-pyridinyl | 4,857,539 |

-continued

| $R_1$ | $R_2$ | $R_5$ | Reference U.S. Pat. No. |
|---|---|---|---|
| 3,5-dichloro | | 1-methyl-1H-pyrrol-2yl | 4,857,539 |
| 3,5-dichloro | | 3-thienyl | 4,857,539 |
| 3,5-dichloro | | 4-pyridinyl | 4,857,539 |
| 3 nitro | H | benzothiazol-2-yl | 4,857,539 |
| H | H | 2-(4,5-dihydro-4 methyl)oxazolyl | 4,843,087 |
| 3 methyl | H | 2-oxazolyl | 4,843,087 |
| 3 bromo | H | 2-oxazolyl | 4,843,087 |
| 3,5-dimethyl | | 3-methyl-5-isoxazolyl | 4,843,087 |
| 2,6-dimethyl | | 3-methyl-5-isoxazolyl | 4,843,087 |
| H | H | 5-methyl-3-isoxazolyl | 4,942,241 |
| H | H | 4-hydroxy phenyl | (Aldrich) |
| H | H | phenyl | (Aldrich) |
| H | H | 5-ethyl-thiazol-2-yl | 5,100,893 |
| H | H | 4,5-dimethyl-thiazol-2-yl | 5,100,893 |
| H | H | 2-ethyl-thiazol-4-yl | 5,100,893 |
| H | H | 5-ethyl-1,3,4-thiadiazol-2-yl | 5,100,893 |
| H | 3-Cl | 3-ethyl-1,2,4-oxadiazol-5-yl | 5,100,893 |
| H | H | 3-cyclopropyl-1,2,4-oxadiazol-5-yl | 5,100,893 |
| H | H | 3-tbutyl-1,2,4-oxadiazolyl | 5,100,893 |
| H | H | 5-ethyl-1,3,4-oxadiazol-2-yl | 5,100,893 |
| H | H | 3-cyclopropyl,2,4-oxadiazol-5-yl | 5,100,893 |
| H | H | 3-ethyl-1,3,4-thiadiazol-5-yl | 5,100,893 |
| H | H | 3-(2hydroxy)propyl-1,2,4-oxadiazol-5-yl | 5,100,893 |
| H | H | 4-ethyl-3-thiazol-2-yl | 5,100,893 |
| H | H | 5-ethyl-3-thiazol-2-yl | 5,100,893 |
| 3-chloro | H | 3-ethyl-1,2,4-oxadiazol-5-yl | 5,100,893 |
| H | H | 4,5-dimethyl-3-thiazol-2-yl | 5,100,893 |
| 2-methoxy | H | 4,5dihydro oxazol-2-yl | 4,843,087 |
| 3-methoxy | H | 4,5dihydro oxazol-2-yl | 4,843,087 |
| 3-chloro | H | 4,5dihydro oxazol-2-yl | 4,843,087 |
| 3-hydroxy | H | 4,5dihydro oxazol-2-yl | 4,843,087 |
| 3,5-di-t-butyl | | 4,5dihydro oxazol-2-yl | 4,843,087 |
| 3-difluoromethyl | H | 4,5dihydro oxazol-2-yl | 4,843,087 |
| 3-hydroxymethyl | H | 4,5dihydro oxazol-2-yl | 4,843,087 |
| 3-carboxy | H | 4,5dihydro oxazol-2-yl | 4,843,087 |
| 2-methyl | 3-hydroxy | 4,5dihydro oxazol-2-yl | 4,843,087 |
| 2,6-dichloro | | 4,5dihydro oxazol-2-yl | 4,843,087 |
| 3,5-dichloro | | 4,5dihydro oxazol-2-yl | 4,843,087 |
| 3-chloro | 5-ethynyl | 4,5dihydro oxazol-2-yl | 4,843,087 |

Example 23

It is contemplated that any of the furans disclosed in U.S. Pat. No. 4,857,539 and 4,861,791 can be used as starting materials for preparing compounds of formula I. Examples of these furans follow; numbering of rings is the same as in other examples, all furans are furans (attached at the [x]position) where $R_4$ is Hydrogen and y is of the formula $(CH_2)n$

|   | n = R1 | $R_2$ $R_3$ | | X = $R_5$ | |
|---|---|---|---|---|---|
| a | 5 H | H | 5 acetyl | 2 | Ethoxy carbonyl |
| b | 5 H | H | 5 acetyl | 2 | 2-4,5dihydrooxazole |
| c | 7 H | H | H | 2 | 2-4,5dihydrooxazole |
| d | 5 3-bromo | H | 5 acetyl | 2 | 2-4,5dihydrooxazole |
| e | 5 3,5-dichloro | | H | 2 | 2-4,5dihydrooxazole |
| f | 5 3,5-dichloro | | H | 2 | 3-4,5dihydrooxazole |
| g | 5 H | H | H | 2 | Ethoxy carbonyl |
| h | 7 H | H | H | 2 | Ethoxy carbonyl |
| i | 5 3,5-dimethyl | | 5-hydroxy-methyl | 2 | 2-methyl-5-tetrazol-yl |
| j | 5 3,5-dimethyl | | 2 acetyl | 3 | 2-methyl-5-tetrazol-yl |
| k | 5 3,5-dimethyl | | 5 acetyl | 2 | 2-methyl-5-tetrazol-yl |
| l | 6 H | H | H | 2 | 2-methyl-5-tetrazol-yl |
| m | 5 3,5-dimethyl | | 5-ethoxy | 2 | 2-methyl-5-tetrazol-yl |
| n | 3 3,5-dimethyl | | 5-acetyl | 2 | 2-methyl-5-tetrazol-yl |
| o | 5 3,5-dimethyl | | 5-formyl | 2 | 2-methyl-5-tetrazol-yl |
| p | 3 3,5-dimethyl | | 5-methyl | 2 | 2-methyl-5-tetrazol-yl |
| q | 2 H | H | H | 2 | 2-methyl-5-tetrazol-yl |
| r | 3 3,5-CH$_3$ | | 5-ethyl | 2 | 2-methyl-5-tetrazol-yl |
| s | 2 3-NO$_2$ | H | 5-(2 methyl-5-isoxazolyl) | 2 | 2-benzothiazole |
| t | 2 H | H | 5-(2 methyl-5-isoxazolyl) | 2 | 2 methyl 5 tetrazolyl |
| u | 3 3,5-dimethyl | | 5-acetyl | 2 | 5-methyl-1,2,4-oxadiazolyl |
| v | 3 3,5-dimethyl | | 3-acetyl | 2 | 5-methyl-1,2,4-oxadiazolyl |
| w | 3 3,5-dimethyl | | 3-acetyl | 2 | 5-methyl-1,2,4-oxadiazolyl |
| x | 3 3,5-dimethyl | | 3-propionyl | 2 | 5-methyl-1,2,4-oxadiazolyl |
| y | 3 3,5-dimethyl | | 5-propionyl | 2 | 5-methyl-1,2,4-oxadiazolyl |
| z | 3 3,5-dimethyl | | 4 acetyl | 2 | 5-methyl-1,2,4-oxadiazolyl |
| aa | 3 3,5-dimethyl | | 5 methoxy carbonyl | 2 | 5-methyl-1,2,4-oxadiazolyl |
| bb | 3 3,5-dimethyl | | 5 cyano | 2 | 5-difluoromethyl-1,2,4-oxadiazlyl |

Biological Evaluation

Biological evaluation of representative compounds of formula I has shown that they possess antipicornaviral activity. They are useful in inhibiting picornavirus replication in vitro and are primarily active against picornaviruses, including enteroviruses, echovirus and coxsackie virus, especially rhinoviruses. The in vitro testing of the representative compounds of the invention against picornaviruses showed that viral replication was inhibited at minimum inhibitory concentrations (MIC) ranging from 0.033 to 0.659 micrograms per milliliter (μg/mL).

The MIC values were determined by an automated tissue culture infectious dose 50% (TCID-50) assay. HeLa cells in monolayers in 96-well cluster plates were infected with a dilution of picornavirus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from picornavirus-induced CPE relative to an untreated picornavirus control.

In the above test procedures, representative compounds of formula I were tested against some the serotypes from either a panel of fifteen human rhinovirus (HRV) serotypes, (noted in the table as panel T) namely, HRV-2, -14, -1A, -1B, -6, -21, -22, -15, -25, -30, -50, -67, -89, -86 and -41 or against some of the serotypes from a panel of 10 human rhinovirus serotypes namely HRV-3, -4, -5, -9, -16, -18, -38, -66, -75 and -67, (noted in the table as panel B) and the MIC value, expressed in micrograms per milliliter (mg/mL), for each rhinovirus serotype was determined for each picornavirus. Then $MIC_{50}$ and $MIC_{80}$ values, which are the minimum concentrations of the compound required to inhibit 50% and 80%, respectively, of the tested serotypes were determined. The compounds tested were found to exhibit antipicornaviral activity against one or more of these serotypes.

The following Table gives the test results for representative compounds of the invention. The panel of picornaviruses used in the test appears before the the $MIC_{80}$ and $MIC_{50}$ figure and the number of serotypes which the compound is tested against (N) is indicated after the $MIC_{80}$ and $MIC_{50}$ figure.

TABLE

| Ex | Panel | $Mic_{50}$ | $Mic_{80}$ | N |
|---|---|---|---|---|
| 1c | T | 0.241 | 0.272 | 15 |
| 1d | T | 0.459 | 2.216 | 10 |
| 2c | T | 0.475 | 0.83 | 2 |
| 2f | B | 0.1315 | — | 10 |
| 2g | B | 0.071 | — | 7 |
| 3a | B | 0.446 | 3.087 | 10 |
| 3b | B | 0.659 | — | 7 |
| 3c | B | 0.074 | 0.129 | 10 |
| 4e | T | 0.453 | — | 15 |
| 5a | T | 0.313 | — | 10 |
| 5e | B | 0.0555 | 0.116 | 10 |
| 6d | B | 0.033 | 0.067 | 9 |
| 7g | B | 0.078 | — | 7 |
| 8e | B | 0.07 | 0.189 | 9 |
| 8g | B | 0.1405 | 0.17 | 10 |
| 8i | B | 0.02 | 0.07 | 10 |
| 9d | T | 0.128 | 0.25 | 6 |
| 9f | T | 0.05 | 0.44 | 10 |
| 10a | T | 0.453 | 99 | 11 |
| 10b | T | 0.055 | 0.098 | 14 |
| 11a | T | 0.453 | — | 11 |
| 11g | T | 0.068 | 0.161 | 14 |

TABLE-continued

| Ex | Panel | $Mic_{50}$ | $Mic_{80}$ | N |
|---|---|---|---|---|
| 12c | B | 0.26 | 1.414 | 7 |
| 12f | B | 0.515 | 0.103 | 10 |
| 12g | B | 0.036 | 0.117 | 10 |
| 12h | B | 0.05 | 0.11 | 10 |
| 12i | B | 0.23 | 0.63 | 9 |
| 12j | B | 0.05 | 0.19 | 9 |
| 12k | B | 0.14 | 0.40 | 9 |
| 12l | B | 0.08 | 0.16 | 10 |
| 12m | B | 0.64 | — | 10 |
| 13f | B | 0.14 | 0.67 | 10 |
| 14p | B | 0.01 | — | 10 |
| 15b | B | 0.03 | 0.15 | 10 |
| 15c | B | 0.29 | — | 8 |
| 15d | B | 0.09 | 0.28 | 10 |
| 16d | B | 0.05 | 2.16 | 9 |
| 16e | B | 0.02 | 0.03 | 10 |
| 16f | B | 0.02 | 0.05 | 10 |
| 16g | B | 0.05 | 0.18 | 10 |
| 16h | B | 0.03 | 0.15 | 10 |
| 16k | B | 0.03 | 0.67 | 9 |
| 16l | B | 0.20 | — | 10 |
| 17d | B | 0.03 | 0.10 | 10 |
| 18c | B | 0.58 | — | 9 |
| 19e | B | 0.08 | 0.44 | 10 |
| 19h | B | — | — | 10 |
| 19i | B | — | — | 8 |
| 20f | B | 0.02 | 0.06 | 10 |
| 20g | B | 0.04 | 0.19 | 10 |
| 20h | B | 0.10 | 0.31 | 8 |
| 20i | B | 0.05 | 0.15 | 10 |
| 20j | B | 0.04 | 0.13 | 10 |
| 21a | B | 0.15 | 1.39 | 10 |
| 21b | B | 0.05 | 0.33 | 9 |
| 21c | B | 0.01 | 0.03 | 9 |
| 21d | B | 0.02 | 0.44 | 9 |
| 21f | B | 0.10 | 0.14 | 9 |
| 21g | B | 0.15 | 0.44 | 10 |
| 21h | B | 0.07 | 0.18 | 10 |

The compounds of formula I can be formulated into compositions, including sustained release compositions together with one or more non-toxic physiologically acceptable carriers, adjuvants or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as an aerosal, for example as a nasal or a buccal spray.

Compositions suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, polyalkylene glycols and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carborymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms can also comprise buffering agents.

Certain solid dosage forms can be delivered through the inhaling of a powder manually or through a device such as a SPIN-HALER used to deliver disodium cromoglycate (INTAL). When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also be formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They can contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations can be prepared as a base for liquid formulations. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, can contain suspending agents, as for example, ethoxylated isostearyl alcohols, polyoxyethylene sorbitol, polyethyleneglycols of varying molecular weights and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in usefule droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or a alkyl chloride, such as methyl, ethyl, or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. Typically, one uses a cosolvent, such as an ether, alcohol or glycol in such aerosol formulations.

The specifications for unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for ingestion or, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses and the like. An effective but non-toxic quantity of the compound is employed in treatment. The dosage of the compound used in treatment depends on the route of administration, e.g., intra nasal, intra bronchial, and the potency of the particular compound.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

It will be appreciated that the starting point for dosage determination, both for prophylaxis and treatment of picornaviral infection, is based on a plasma level of the compound at roughly the minimum inhibitory concentration levels determined for a compound in the laboratory. For example a MIC of 1 μg/mL would give a desired starting plasma level of 0.1 mg/dl and a dose for the average 70 Kg mammal of roughly 5 mg. It is specifically contemplated that dosage range may be from 0.01–1000 mg.

Actual dosage levels of the active ingredient in the compositions can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors and is readily determined by those skilled in the art.

The formulation of a pharmaceutical dosage form, including determination of the appropriate ingredients to employ in formulation and determination of appropriate levels of active ingredient to use, so as to achieve the optimum bioavailability and longest blood plasma halflife and the like, is well within the purview of the skilled artisan, who normally considers in vivo dose-response relationships when developing a pharmaceutical composition for therapeutic use.

Moreover, it will be appreciated that the appropriate dosage to achieve optimum results of therapy is a matter well within the purview of the skilled artisan who normally considers the dose-response relationship when developing a regimen for therapeutic use. For example the skilled artisan may consider in vitro minimum inhibitory concentrations as a guide to effective plasma levels of the drug. However, this and other methods are all well within the scope of practice of the skilled artisan when developing a pharmaceutical.

It will be understood that the specific dose level for any particular patient will depend upon a variety of factors including the body weight, general health, sex, diet, time and route of administration, rates of absorption and excretion, combination with other drugs and the severity of the disease being treated and is readily determined by the skilled clinician.

When administered prior to infection, that is, prophylactically, it is preferred that the administration be within about 0 to 48 hours prior to infection of the host animal with the pathogenic picornavirus. When administered therapeutically to inhibit an infection it is preferred that the administration be within about a day or two after infection with the pathogenic virus.

The dosage unit administered will be dependent upon the picornavirus for which treatment or prophylaxis is desired, the type of animal involved, its age, health, weight, extent of infection, kind of concurrent treatment, if any, frequency of treatment and the nature of the effect desired.

The compound of the invention also finds utility in preventing the spread of picornaviral infection. The compounds can be used in aerosol sprays applied to contaminated surfaces, to disposable products, such as tissues and the like used by an infected person. In addition the compounds can be used to impregnate household products such as tissues, other paper products, disposable swabs, and the like to prevent the spread of infection by inactivating the picornavirus.

Because compounds of the invention are able to suppress the growth of picornaviruses when added to a medium in which the picornavirus is growing, it is specifically contemplated that compounds of the invention can be used in disinfecting solutions, for example in aqueous solution with a surfactant, to decontaminate surfaces on which polio, Coxsackie, rhinovirus and/or other are present, picornaviruses such surfaces including, but not limited to, hospital glassware, hospital working surfaces, restaurant tables, food service working surfaces, bathroom sinks and anywhere else that it is expected that picornaviruses may be harbored.

Hand contact of nasal mucus may be the most important mode of rhinovirus transmission. Sterilization of the hands of people coming into contact with persons infected with rhinovirus prevents further spread of the disease. It is contemplated that a compound of the invention incorporated into a hand washing or hand care procedure or product, inhibits production of rhinovirus and decreases the likelihood of the transmission of the disease.

We claim:

1. A compound of formula:

$$R_3 \underset{O}{\overset{R_4}{\diagdown}} Y-O-\underset{R_2}{\overset{R_1}{\diagdown}} R_5$$

wherein:

Y is an alkylene bridge of 3–9 carbon atoms;

$R_1$ and $R_2$ are each individually chosen from hydrogen, halo, amino, hydroxyhaloalkyl, alkylthioalkyl, alkylsulfinylalkyl, alkylsulfonyl, alkylaminoalkyl, alkyl, alkenyl, amino, alkylthio, hydroxy, dialkylaminoalkyl, cyanomethyl, alkoxy, nitro, carboxy, alkoxycarbonyl, difluoromethyl, alkynyl, trifluoromethyl or cyano;

$R_3$ and $R_4$ are each independently chosen from hydrogen, alkyl, alkoxy, hydroxy, cycloalkyl, hydroxyalkyl, alkoxyalkyl, hydroxyalkoxy, alkylthioalkyl, alkanoyl, alkanoyloxy, alkylsulfinylalkyl, alkylsulfonylalkyl, aminoalkyl, alkylaminoalkyl, dialkylaminoalkyl, alkoxycarbonyl, carboxy, cyanomethyl, fluoroalkyl, cyano, phenyl, alkynyl, alkoxy, or halo;

$R_5$ is alkoxycarbonyl, phenyl, or substituted phenyl wherein the substitution is with alkyl, alkoxyalkyl, cycloalkyl, haloalkyl, halo, hydroxyalkyl, alkoxy, hydroxy, furyl, thienyl, fluoroalkyl; or a pharmaceutically acceptable acid addition salt thereof.

2. A compound according to claim 1 wherein the furan is attached to Y at the 3 position.

3. A compound of formula:

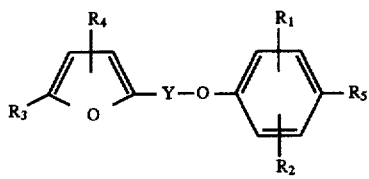

wherein:

Y is an alkylene bridge of 3–9 carbon atoms;

$R_1$ and $R_2$ are each independently chosen from hydrogen, halo, alkenyl, alkyl, alkenyl, alkyenylamino, alkylthio, hydroxyhaloalkyl, hydroxy, hydroxyalkyl, alkoxyalkyl, alkylthioalkyl, alkylsulfinylalkyl, alkylsulfonylalkyl, alkoxy, nitro, carboxy, alkoxycarbonyl, aminoalkyl, alkylaminoalkyl, dialkylaminoalkyl, cyanomethyl, difluoromethyl, trifluoromethyl or cyano;

$R_3$ is hydrogen, alkyl, alkoxy, hydroxy, cycloalkyl, hydroxyalkyl, hydroxyhaloalkyl, alkoxyalkyl, hydroxyalkoxy, alkylthioalkyl, alkanoyl, alkanoyloxy, alkylsulfinylalkyl, alkylsulfonylalkyl, aminoalkyl, alkylaminoalkyl, dialkylaminoalkyl, alkoxycarbonyl, carboxy, cyanomethyl, fluoroalkyl, cyano, phenyl, alkynyl, alkenyl, or halo;

$R_4$ is hydrogen or halo; and $R_5$ is alkoxycarbonyl, phenyl, or substituted phenyl wherein the substitution is with alkyl, alkoxyalkyl, cycloalkyl, haloalkyl, hydroxyalkyl, alkoxy, hydroxy, halo, furyl, thienyl, fluoroalkyl; or a pharmaceutically acceptable acid addition salt thereof.

4. A compound according to claim 1 wherein $R_4$ is hydrogen, $R_1$ and $R_2$ are in the 3,5 positions and $R_1$ and $R_2$ are each independently hydrogen, alkyl, halo or cyano.

5. A compound according to claim 2 wherein Y is 1,3-propylene, $R_1$ and $R_2$ are 3,5-dimethyl, and $R_3$ is methyl, ethyl, acetyl, methoxy or difluoromethyl, hydrogen, formyl or propyl.

6. A method of combating picornaviruses comprising contacting the locus of said viruses with a compound of claim 1.

7. A method of combating picornaviruses comprising contacting the locus of said viruses with a compound of claim 3.

* * * * *